(12) United States Patent
Shi et al.

(10) Patent No.: US 11,020,535 B2
(45) Date of Patent: Jun. 1, 2021

(54) INSULIN PEN NEEDLE WITH NEEDLE TIP PROTECTION

(71) Applicant: STERLING MEDICAL (SUZHOU) INC., Suzhou, Jiangsu (CN)

(72) Inventors: Guoping Shi, Suzhou (CN); Anthony Scott Horstman, Suzhou (CN)

(73) Assignee: STERILANCE MEDICAL (SUZHOU) INC., Suzhou (CN)

( * ) Notice: Subject to any disclaimer, the term of this patent is extended or adjusted under 35 U.S.C. 154(b) by 95 days.

(21) Appl. No.: 15/570,521

(22) PCT Filed: Mar. 31, 2016

(86) PCT No.: PCT/CN2016/078194
§ 371 (c)(1),
(2) Date: Oct. 30, 2017

(87) PCT Pub. No.: WO2016/173384
PCT Pub. Date: Nov. 3, 2016

(65) Prior Publication Data
US 2018/0147365 A1    May 31, 2018

(30) Foreign Application Priority Data
Apr. 28, 2015    (CN) .......................... 201510209194.0

(51) Int. Cl.
*A61M 5/32* (2006.01)
*A61M 5/00* (2006.01)
(Continued)

(52) U.S. Cl.
CPC ............ *A61M 5/3202* (2013.01); *A61M 5/32* (2013.01); *A61M 5/321* (2013.01); *A61M 5/326* (2013.01);
(Continued)

(58) Field of Classification Search
CPC ...... A61M 5/3202; A61M 5/32; A61M 5/321; A61M 5/326; A61M 5/002; A61M 5/3271
(Continued)

(56) References Cited

U.S. PATENT DOCUMENTS

| 2005/0277895 | A1* | 12/2005 | Giambattista | ......... A61M 5/002 604/198 |
| 2009/0005742 | A1* | 1/2009 | Liversidge | ............ A61M 5/326 604/263 |

FOREIGN PATENT DOCUMENTS

| CN | 104771815 A | 7/2015 |
| CN | 204995929 U | 1/2016 |

OTHER PUBLICATIONS

Jun. 7, 2016 International Search Report issued in International Patent Application No. PCT/CN2016/078194.

* cited by examiner

*Primary Examiner* — Phillip A Gray
(74) *Attorney, Agent, or Firm* — Oliff PLC

(57) ABSTRACT

An insulin injection needle with needle tip protection has a needle body, needle base, main cover and outer sheath. The main cover is provided with the trigger tube, front casing and spring. The trigger tube is used to protect the injection section of needle body before use and the front casing is used to protect the injection section of needle body after use. Before use, the trigger tube extends out of the main cover and is in the state of protecting the needle, and the front casing is in the main cover; after, the trigger tube is in the main cover and the front casing extends out of the main cover and protects the needle. The unlocking of trigger tube and front casing correlate with injection readiness and the tail cover and needle base trigger the unlocking of trigger tube and front casing during the installation.

14 Claims, 13 Drawing Sheets

(51) Int. Cl.
*A61M 5/34* (2006.01)
*B42D 15/00* (2006.01)
*G09F 1/04* (2006.01)

(52) U.S. Cl.
CPC ............... *B42D 15/00* (2013.01); *G09F 1/04*
(2013.01); *A61M 5/002* (2013.01); *A61M
5/3271* (2013.01); *A61M 5/34* (2013.01);
*A61M 2005/3247* (2013.01); *A61M 2005/3254*
(2013.01); *A61M 2005/3267* (2013.01); *A61M
2205/6063* (2013.01)

(58) Field of Classification Search
USPC ........................................................ 604/192
See application file for complete search history.

INSULIN PEN NEEDLE WITH NEEDLE TIP PROTECTION

TECHNICAL FIELD

The present invention relates to a medical insulin injection tool, especially a disposable safety insulin pen needle with needle tip protection. This injection needle could be used with the insulin pen to inject by oneself or by others, while the insulin pen could be reused and the injection needle is disposable.

BACKGROUND OF INVENTION

Diabetes is a metabolic disease characterized by high blood sugar, and there is no radical cure to it, but the injection of insulin to the patients could effectively control the disease.

The insulin injection tools are diversified and the insulin injection needle mentioned in the present invention is an injection tool used with the insulin pen, which could carry a prescribed amount of insulin liquid medicine and could be reused, while the injection needle is a disposable needle with safety protection device.

Chinese patent CN101563124A discloses a utility patent application with the title of Needle Protection Device with Distal and Proximal Protector, and US patent US2011/0288491A1 discloses an utility patent application with the title of Safety Needle Assembly. These two patents relate to the insulin pen needle and the basic structure includes:
1. Needle body for injecting the insulin and the needle base to fix the needle body;
2. Main cover for connecting the insulin pen;
3. Casing for protecting the needle body before and after the use;
4. Spring for moving the casing;
5. The outer sheath for protecting the entire needle of the injection needle is not shown in the drawings of the two patents, but is visible in the actual product and is generally indispensable.

In the existing injection needles and from the view of protection structure of needle body, the former injection needle is provided with a front end protection structure and a rear end protection structure and the latter injection needle is only provided with a front end protection structure. The invention designs a new type of insulin injection needle with needle tip protection from the view of safety and convenience.

DISCLOSURE OF THE INVENTION

The present invention provides a new type of insulin injection needle with needle tip protection, which is intended to enrich the product types of insulin pen needle and improve the product performance of insulin pen needle.

In order to achieve the above purpose, the present invention applies the first technical solution (with front end and rear end protection): a kind of insulin injection needle with needle tip protection includes:
A needle body having an injection section extending in a forward direction, a connecting section extending in a rearward direction and a fixing section between the injection section and the connecting section;
A needle base used to fix the needle body, and the fixing section of needle body is fixed on the needle base, the injection section of needle body extends from the front end of needle base and the connecting section of needle body extends from the rear end of needle base;
A main cover consisting of the cylindrical structure in which the needle base and needle body are located under the assembly state, and the rear end of main cover is connected to the insulin pen;
Wherein:
The needle base consists of a seat plate and a seat rod and the seat rod is located in the front end of seat plate and connected with the seat plate in a fixed way; the seat plate is provided with two dodging grooves and the outer edge of the seat plate matches with the inner edge of the main cover, and the outer edge of corresponding seat plate has a first positioning position and a second positioning position on the inner edge of main cover in the axial direction; during the installation of injection needle to the insulin pen, it uses the axial thrust of insulin pen head to the needle base to push the seat plate in the main cover to move from the first positioning position to the second positioning position in the axial direction to form the sliding positioning connection relationship between the needle base and main cover; the outer edge of seat plate in the first positioning position matches with inner edge of main cover through the first positioning structure and the outer edge of seat plate in the second positioning position matches with inner edge of main cover through the second positioning structure; the first positioning structure is a concavo-convex positioning structure, an elastic positioning structure, or a frictional positioning structure; and the second positioning structure is a concavo-convex positioning structure, an elastic positioning structure, a friction positioning structure, a locking positioning structure or an end face abutment positioning structure;
The inner wall of main cover is provided with a first tenon stage in the middle, a second tenon stage in the front end and a third tenon stage in the rear end and is provided with a anti-back slot in the forepart;
The main cover is provided with tail cover, front casing, trigger tube and spring;
The tail cover consists of a cap and two front legs; the cap is an end cap or a ring body and the center of the cap is provided with a needle hole for only inserting the needle body connecting section so that the needle hole axis is parallel to the main cover axis; the two front legs are fixedly attached to the front end of cap and are arranged symmetrically with reference to the needle hole axis, and the inner side of each front leg is provided with a bevel at the root position, a stopper extending inward in the middle and a foot hook in the end position; the outer side of each front leg is provided with a sharp tenon in the middle;
The main structure of front casing is the tubular body and the front casing is provided with an inner end face at the inner side of front end; the front casing is provided with a flexible tenon extending backward and a flexible tail fin extending backward, and the flexible tenon and the flexible tail fin are arranged in a staggered way circumferentially; the front casing is provided with a convex extending outward at the outer side in the middle and the convex and the flexible tenon are in the corresponding position in the circumferential direction and the convex is provided with a bevel at the side of flexible tenon;
The main structure of trigger tube is the tubular body and the trigger tube is provided with two inserts extending backward at the rear end and the insert is provided with a barb; a recess is set between the tubular body of trigger tube and seat rod at one side and a convex is set at the other side and the recess contacts the convex to form a third positioning;

Under the assembly state before the use, the seat plate is located in the first positioning position in the main cover, the tail cover is located in the rear end of main cover, the cap on the tail cover is located in the back of seat plate to protect the connecting section of needle body and the two front legs on the tail cover extends through the two dodging slots of the seat plate to the front; the front casing is located in the main cover, and the flexible tenon of the front casing is in the first tenon stage of main cover to limit the forward movement of front casing in relative to the main cover and the foot hooks of two front legs of the tail cover hook the flexible tenons of front casing; the trigger tube is located in the front end of main cover and extends out of the front end to protect the injection section of needle body and the trigger tube is provided with the limit position for forward movement in relative to the main cover and the rear part of trigger tube is fixed on the seat rod of needle base, the rear of trigger tube is located in the front casing, the trigger tube is located in the third positioning position and the seat plate of needle base is located in the first positioning position in relative to the main cover, the spring is against the stopper of two front legs of tail cover at one end and against the inner end face of front casing at the other end;

During the use and when the injection needle is installed to the insulin pen, the head of insulin pen pushes the tail cover to move forward, the foot hook of tail cover is lifted by the bevel of convex of front casing, and then passes over the convex, and the bevel of tail cover presses the flexible tenon inward to finally force the flexible tenon to unhook from the first tenon stage to release the limit of forward movement of front casing in the main cover and at the same time, the front casing is moved forward by the spring until the convex is stopped by the foot hook to limit the forward movement of front casing; then, the cap of the tail cover contacts the seat plate of needle base and pushes the seat plate to move forward from the first positioning position to the second positioning position, and as the trigger tube is limited by the forward movement limit, when the needle base moves forward, the trigger tube and the seat rod release the third positioning and form the sliding connection; then, when the frond end of trigger tube contact the skin of human body, the trigger tube moves backward and the insert of the trigger tube lifts the stopper on the tail cover to force the foot hook of tail cover to gradually separate from the convex of front casing until it's fully separated, so the front casing moves forward by the spring and extends through the front end of main cover and the front end of front casing is blocked by the skin of human body and moves together with the front end of trigger tube until the needle is penetrated into the skin to inject the insulin;

When the injection needle is pulled out from the skin after the use, the front casing is pushed out of the front end of main cover by the spring until the convex of front casing is stopped by the second tenon stage on the main cover, and at this time, the front casing is used to protect the injection section of needle body; at the same time, the flexible tail fin of front casing expands and is stuck in the anti-back slot of main cover to form the limit for the backward movement of front casing to prevent the returning of front casing;

When the injection needle is removed from the head of insulin pen after the use, the tail cover moves backward by the spring and the two stoppers on the tail cover hold the inserts of trigger tube to move the trigger tube backward until the front end of seat rod on the needle base contacts the inner end face of trigger tube to stop; then the sharp tenon on the tail cover falls in the third tenon stage of main cover to form the limit for forward movement of tail cover, and the barbs of inserts of trigger tube match the stoppers to limit the backward movement of tail cover in the back of main cover, and at this time, the tail cover is used to protect the connecting section of needle body and prevent the repeated use of injection needle.

In order to achieve the above purpose, the present invention applies the second technical solution (only with front end protection): a kind of insulin injection needle with needle tip protection includes:

A needle body having an injection section extending in a forward direction, a connecting section extending in a rearward direction and a fixing section between the injection section and the connecting section;

A needle base used to fix the needle body, and the fixing section of needle body is fixed on the needle base, the injection section of needle body extends from the front end of needle base and the connecting section of needle body extends from the rear end of needle base;

A main cover consisting of the cylindrical structure in which the needle base and needle body are located under the assembly state, and the rear end of main cover is connected to the insulin pen;

Wherein:

The needle base consists of a seat plate, a seat rod and two front legs; and the seat rod is located in the front end of seat plate and connected with the seat plate in a fixed way; the two front legs are arranged symmetrically at two sides of the seat rod and the roots of two front legs are fixedly attached to the seat plate, and the inner side of each front leg is provided with a bevel at the root position, a stopper extending inward in the middle and a foot hook in the end position; and the outer edge of the seat plate matches with the inner edge of the main cover, and the outer edge of corresponding seat plate has a first positioning position and a second positioning position on the inner edge of main cover in the axial direction; during the installation of injection needle to the insulin pen, it uses the axial thrust of insulin pen head to the seat plate to push the seat plate in the main cover to move from the first positioning position to the second positioning position in the axial direction to form the sliding positioning connection relationship between the needle base and main cover; the outer edge of seat plate in the first positioning position matches with inner edge of main cover through the first positioning structure and the outer edge of seat plate in the second positioning position matches with inner edge of main cover through the second positioning structure; the first positioning structure is a concavo-convex positioning structure, an elastic positioning structure, or a frictional positioning structure; and the second positioning structure is a concavo-convex positioning structure, an elastic positioning structure, a friction positioning structure, a locking positioning structure or an end face abutment positioning structure;

The inner wall of main cover is provided with a first tenon stage in the middle, a second tenon stage in the front end and is provided with a anti-back slot in the forepart;

The main cover is provided with front casing, trigger tube and spring;

The main structure of front casing is the tubular body and the front casing is provided with an inner end face at the inner side of front end; the front casing is provided with a flexible tenon extending backward and a flexible tail fin extending backward, and the flexible tenon and the flexible tail fin are arranged in a staggered way circumferentially; the front casing is provided with a convex extending outward at the outer side in the middle and the convex and the flexible tenon are in the corresponding position in the circumferential direction;

The main structure of trigger tube is the tubular body and the trigger tube is provided with two inserts extending backward at the rear end and the insert is provided with a barb; a recess is set between the tubular body of trigger tube and seat rod at one side and a convex is set at the other side and the recess contacts the convex to form a third positioning;

Under the assembly state before the use, the seat plate is located in the first positioning position in the main cover, and the two front legs on the seat plate extending forward extend to the front; the front casing is located in the main cover, and the flexible tenon of the front casing is in the first tenon stage of main cover to limit the forward movement of front casing in relative to the main cover; the trigger tube is located in the front end of main cover and extends out of the front end to protect the injection section of needle body and the trigger tube is provided with the limit position for forward movement in relative to the main cover and the rear part of trigger tube is fixed on the seat rod of needle base, the rear of trigger tube is located in the front casing, the trigger tube is located in the third positioning position and the seat plate of needle base is located in the first positioning position in relative to the main cover; the spring is against the stopper of two front legs of needle base at one end and against the inner end face of front casing at the other end;

During the use and when the injection needle is installed to the insulin pen, the head of insulin pen pushes the seat plate to move forward, and the bevel of inner side of front leg presses the flexible tenon inward to finally force the flexible tenon to unhook from the first tenon stage to release the limit of forward movement of front casing in the main cover and at the same time, the front casing is moved forward by the spring until the convex is stopped by the foot hook to limit the forward movement of front casing; then, the seat plate moves forward from the first positioning position to the second positioning position, and as the trigger tube is limited by the forward movement limit, when the needle base moves forward, the trigger tube and the seat rod release the third positioning and form the sliding connection; at the same time, when the frond end of trigger tube contact the skin of human body, the trigger tube moves backward and the insert of the trigger tube lifts the stopper on the front leg to force the foot hook of front leg to gradually separate from the convex of front casing until it's fully separated, so the front casing moves forward by the spring and extends through the front end of main cover and the front end of front casing is blocked by the skin of human body and moves together with the front end of trigger tube until the needle is penetrated into the skin to inject the insulin;

When the injection needle is pulled out from the skin after the use, the front casing is pushed out of the front end of main cover by the spring until the convex of front casing is stopped by the second tenon stage on the main cover, and at this time, the front casing is used to protect the injection section of needle body; at the same time, the flexible tail fin of front casing expands and is stuck in the anti-back slot of main cover to form the limit for the backward movement of front casing to prevent the returning of front casing, and finally the injection needle is removed from the head of insulin pen.

The above described technical solution is explained as follows:

1. In the present invention, the "front" in the "front end", "forward", "front and back", "front part", "forward direction", "front" and "front end face" refers to the direction of the needle tip of the injection section of disposable insulin pen needle pointing to. The "rear" in said "rear end", "front and back", "backwards", "rear part" means the direction opposite to the "front".

2. In above described technical solution, the concavo-convex positioning structure is formed by a groove provided in the circumferential direction of the outer edge of seat plate and a protruding rib provided on the inner edge of the main cover.

3. In above described technical solution, the elastic positioning structure is formed by matching of an elastic bead pin and a pitting; among the elastic bead pin and pitting, one is set in the outer edge of seat plate and the other is set in the inner edge of main cover.

4. In above described technical solution, the friction positioning structure is formed by the friction matching of outer edge of seat plate and inner edge of main cover.

5. In above described technical solution, the locking positioning structure is formed by the matching of outer edge and front and rear of seat plate and the slot at the inner edge of main cover.

6. In above described technical solution, the end face abutment positioning structure is formed by the abutment matching of front end at the outer edge of seat plate and the inner end face at the inner edge of main cover.

7. In above described technical solution, the main cover is provided with an outer sheath, which is a sleeve structure, and the outer sheath is installed at the outside of main cover under the assembly state before use to protect the injection needle; the trigger tube is provided with a forward movement limit relative to the main cover, which is formed by the front end of the trigger tube being close to or abutted against the front inner end face of the outer sheath.

The design principle and effect of present invention is: the present invention relates to an insulin injection needle with needle tip protection, wherein the first technical solution has the front end and rear end protection, while the second technical solution has only the front end protection without the rear end protection. The front end protection utilizes a trigger tube to protect the injection section of needle body before the use and utilizes a front casing to protect the injection section of needle body after the use. Before the use of injection needle, the trigger tube extends out of the main cover and is in the state of protecting the needle, and the front casing is in the main cover; after the use of injection needle, the trigger tube is in the main cover and the front casing extends out of the main cover and is in the state of protecting the needle. The rear end protection utilizes the tail cover set at the rear end of the main cover to protect the connecting section of needle body before and after the use.

The present invention correlates the movement and positioning of trigger tube, front casing, front leg and needle base protecting the needle body and adopts the following measures: Firstly, a third positioning structure formed by a concavo-convex structure is provided between the trigger tube body and the seat rod, and at the same time, the flexible tenon on the front casing is stuck on the first tenon stage on the main cover to limit the forward movement of front casing relative to the main cover. The resolution of reliability issue of trigger tube and front casing protecting the injection section of needle body before and during the use ensures the effective protection of safety of injection section of needle body by the trigger tube and front casing before and during the use;

Secondly, to design the fixing between the needle base of needle body and main cover to the sliding positioning connection relationship, i.e. during the installation of injection needle, it uses the axial thrust of insulin pen head to the needle base to push the seat plate on the needle base to move from the first positioning position to the second positioning position to correlate the information of installation of injection needle with the sliding position of seat plate of needle base in the main cover; and it utilizes the movement of front leg to disconnect the front casing;

Thirdly, the correlation of the information of installation of injection needle with the movement of seat plate in the main cover and unlocking of trigger tube and front casing after the positioning and the correlation of unlocking of trigger tube and front casing after the positioning with the ready injection state of insulin pen and injection needle greatly improve the safety and convenience of injection needle.

In short, the present invention reasonably utilizes the axial thrust and movement of needle base during installation the injection needle to achieve the purpose of automatic unlocking of trigger tube and utilizes the movement of front leg during installation of injection to unlock the front casing and its clever technical concept and reasonable design plan have the outstanding substantive characteristics and significant technological progress, highlighting the safety and convenience of injection needle.

Figure 1:
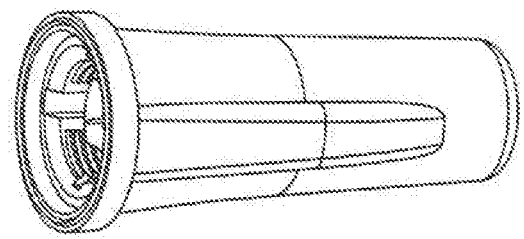
FIG. 1 is the perspective view of the insulin pen needle in the embodiment of present invention.
Figure 2:
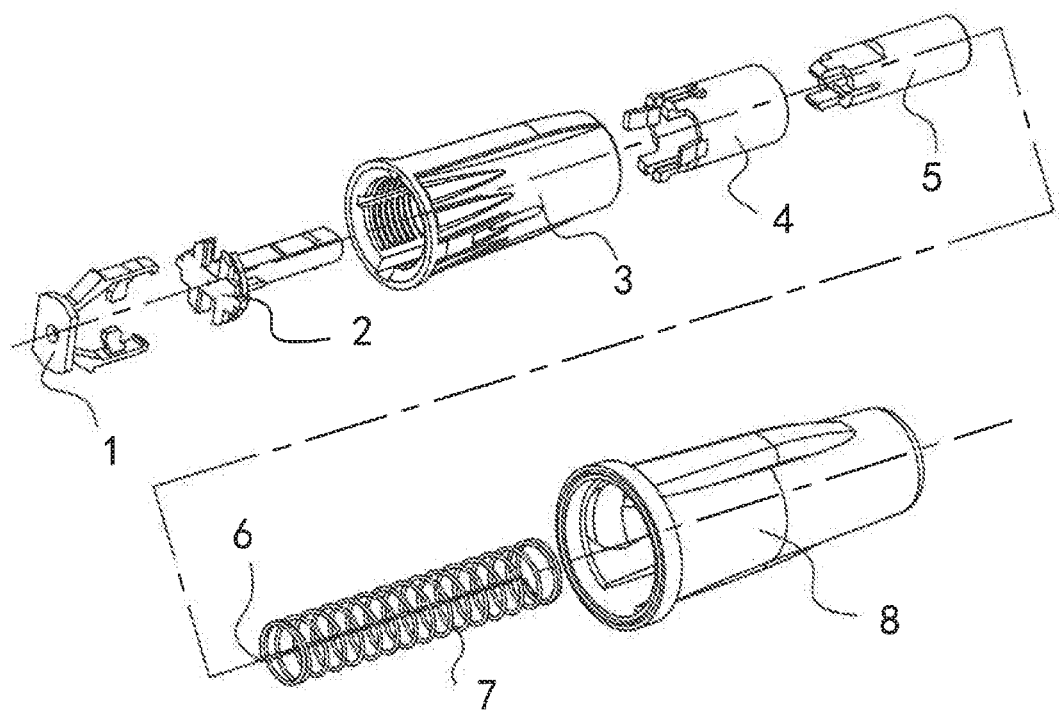
FIG. 2 is the exploded view of the insulin pen needle in the embodiment of present invention.

In the above described drawings:
1. Tail cover; 11. Foot hook; 12. Inclined surface; 13. Block; 14. Sharp tenon; 15. Cap; 16. Front leg; 17. Dodging hole; 2. Needle base; 21. Groove; 22. Convex; 23. Seat plate; 24. Seat rod; 25. Dodging slot;

3. Main cover, 31. First tenon stage; 32. Dodging slot; 33. Protruding rib; 34 Slot; 35. Second tenon stage; 36. Anti-back slot; 37. Third tenon stage; 38. Bayonet; 39. Sliding channel;
4. Front casing; 41. Flexible tenon; 42. Convex; 43. Flexible tail fin; 44. Inner end face; 45. Inclined surface; 46. Wedge;
5. Trigger tube; 51. Recess; 52. Insert; 53. Stopper;
6. Needle body;
7. Spring;
8. Outer sheath; 81. Block; 82. Rib.

SPECIFIC EMBODIMENT

With reference to the accompanying drawings and embodiment, the present invention will be described in detail.

Embodiment 1: Insulin Pen Needle with Front End and Rear End Needle Tip Protection As shown in FIG. 1-10, the injection needle consists of a needle body 6, needle base 2, main cover 3, outer sheath 8, tail cover 1, front casing 4, trigger tube 5 and spring 7 (see FIG. 2).

The following is the description of the components of insulin pen needle in this embodiment:

1. Needle Body 6

The needle body 6 is the needle to inject the insulin and the needle body 6 has an injection section extending in a forward direction, a connecting section extending in a rearward direction and a fixing section between the injection section and the connecting section;

2. Needle Base 2

The needle base 2 is used to fix the needle body 6 (see FIG. 4) and the fixing section of needle body 6 is fixed on the needle base 2, the injection section of needle body 6 extends from the front end of needle base 2 and the connecting section of needle body 6 extends from the rear end of needle base 2; The needle base 2 consists of a seat plate 23 and a seat rod 24 and the seat rod 24 is located in the front end of seat plate 23 and connected with the seat plate 23 in a fixed way; the seat rod 24 is provided with a convex 22 and the seat plate 23 is provided with two dodging grooves 25, and the seat plate 23 is provided with a groove 21 in the circumferential direction.

3. Main Cover 3

Figure 5:
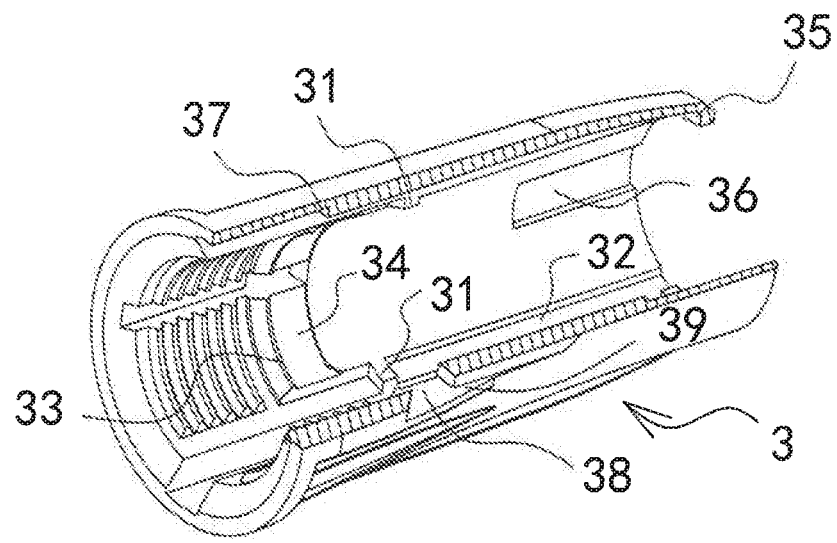
FIG. 5 is the perspective view of the main cover with local view in the embodiment of present invention.

The main cover 3 is used to accommodate all components excluding the outer sheath 8 (see FIG. 5). The main cover 3 is the cylindrical structure and the needle base 2 and the needle body 6 are located in the main cover 3 under the assembly state. The inner wall of main cover 3 is provided with a first tenon stage 31 in the middle, a second tenon stage 35 in the front end and a third tenon stage 37 in the rear end and is provided with a anti-back slot 36 in the forepart and a dodging slot 32 in the forepart; the inner edge of main cover 3 is provided with a protruding rib 33 and slot 34, and the protruding rib 33 is located in the first positioning position in axial direction of main cover 3 and the slot 34 is located in the second positioning position in axial direction of main cover 3, and the distance from the first positioning position to the rear end of the main cover 3 is smaller than the distance from the second positioning position to the rear end of the main cover 3 based on rear end of main cover 3. The side wall of main cover 3 is provided with a bayonet 38, and the bayonet 38 is located in the second positioning position in axial direction of main cover 3 and the bayonet 38 is the through hole between the inner wall and outer wall of main cover 3 and the bayonet 38 is provided with a sliding channel 39 extending in the front end direction (to facilitate disconnection of the block 81 and the bayonet 38). The rear end of main cover 3 is used to connect the insulin pen and the connection structure may be the screw connection, plug-in connection and plug-in turn buckle connection, etc. In this embodiment, the main cover 3 in FIG. 5 is the screw connection.

4. Outer Sheath 8

Figure 10:
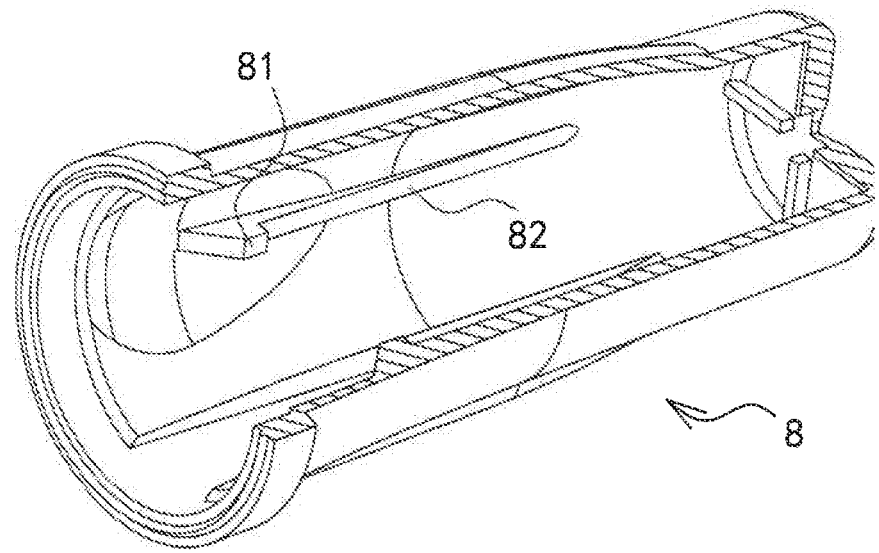
FIG. 10 is the perspective view of the outer sheath with local view in the embodiment of present invention.
Figure 11:
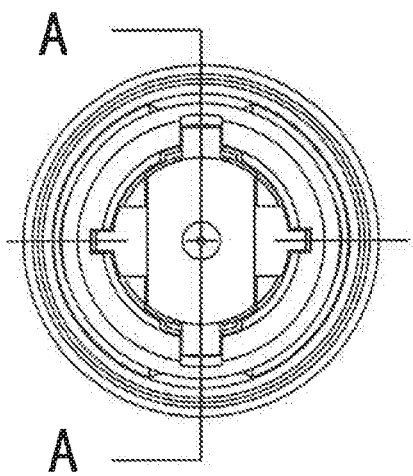
FIG. 11 is the end view of an insulin injection needle with A-A section in the embodiment of the present invention.
Figure 12:
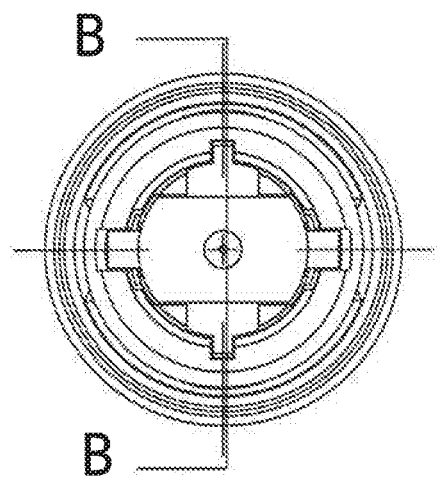
FIG. 12 is the end view of an insulin injection needle with B-B section in the embodiment of the present invention.
Figure 13:
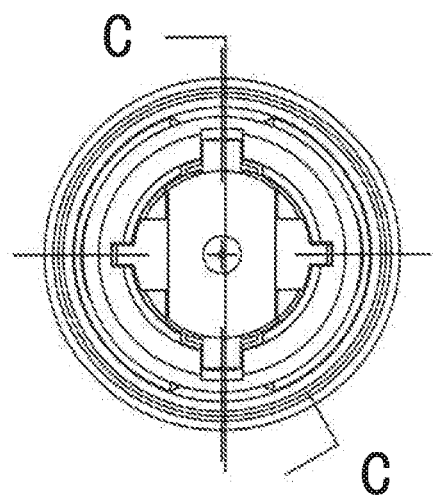
FIG. 13 is the end view of an insulin injection needle with C-C section in the embodiment of the present invention.

The outer sheath 8 is used to protect the injection needle (see FIG. 10). The outer sheath 8 is a sleeve structure and the outer sheath 8 is installed at the outside of main cover 3 under the assembly state before use. The inner side of sleeve of outer sheath 8 is provided with a block 81, and the position of block 81 is corresponding to the bayonet 38 at the side wall of main cover 3, and when the outer sheath 8 is installed at the main cover 3, the block 81 is stuck in the bayonet 38 and extends into the main cover 3 to form the locking connection of outer sheath 8 and main cover 3. The inner wall of sleeve of outer sheath 8 is provided with the rib 82 protruding inward in axial direction and when the outer sheath 8 is installed at the outside of main cover 3, there is gap for deformation of outer sheath 8 between the inner wall of outer sheath 8 and outer wall of main cover 3.

5. Tail Cover 1

Figure 3:
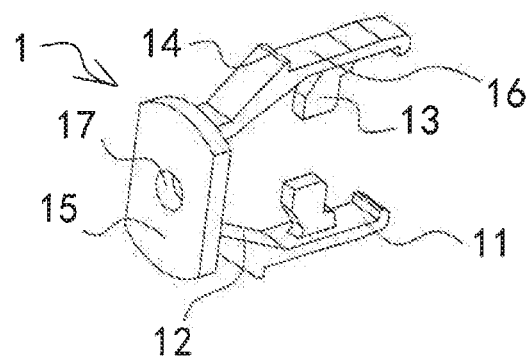
FIG. 3 is the perspective view of the tail cover in the embodiment of present invention.
Figure 4:
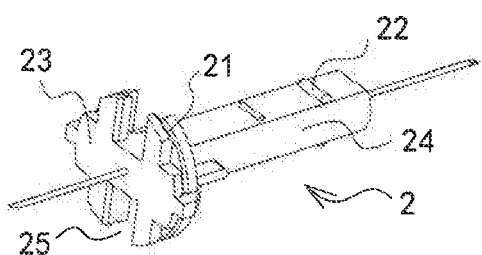
FIG. 4 is the perspective view of the needle base and needle body in the embodiment of present invention.

The tail cover 1 is used to protect the connecting section of needle body 6 (see FIG. 3). The tail cover 1 consists of a cap 15 and two front legs 16; the cap 15 is an end cap or a ring body and the center of the cap 15 is provided with a needle hole 17 for only inserting the needle body 6 connecting section so that the needle hole 17 axis is parallel to the main cover 3 axis; the two front legs 16 are fixedly attached to the front end of cap 15 and are arranged symmetrically with reference to the needle hole 17 axis, and the inner side of each front leg 16 is provided with a bevel 12 at the root position, a stopper 13 extending inward in the middle and a foot hook 11 in the end position; the outer side of each front leg 16 is provided with a sharp tenon 14 in the middle.

6. Front Casing 4

Figure 6:
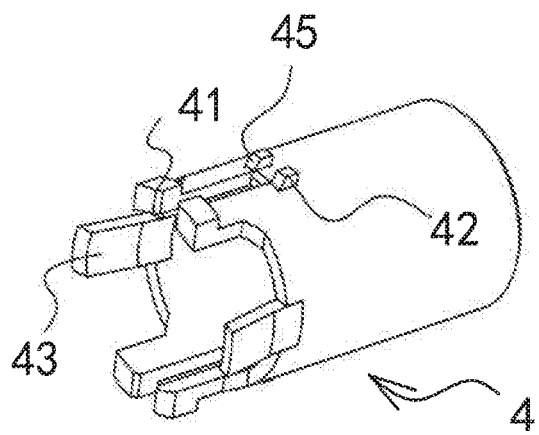
FIG. 6 is the perspective view of the front casing in the embodiment of present invention.
Figure 7:
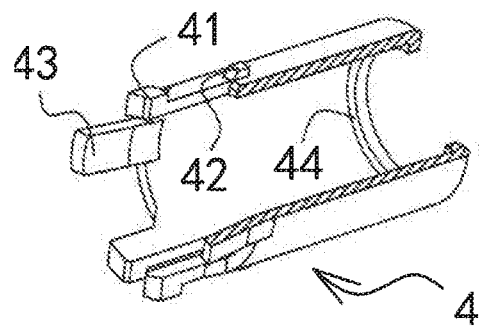
FIG. 7 is the perspective view of the front casing with local view in the embodiment of present invention.

The front casing 4 is used to protect the injection section of needle body 6 after use (see FIGS. 6 and 7). The main structure of front casing 4 is the tubular body and the front casing 4 is provided with an inner end face 44 at the inner side of front end; the front casing 4 is provided with a flexible tenon 41 extending backward and a flexible tail fin 43 extending backward, and the flexible tenon 41 and the flexible tail fin 43 are arranged in a staggered way in the circumferential direction of front casing 4; the front casing 4 is provided with a convex 42 extending outward at the outer side in the middle and the convex 42 and the flexible tenon 41 are in the corresponding position in the circumferential direction of front casing 4 and the convex 42 is provided with a bevel 45 at the side of flexible tenon 41.

7. Trigger Tube 5

Figure 8:
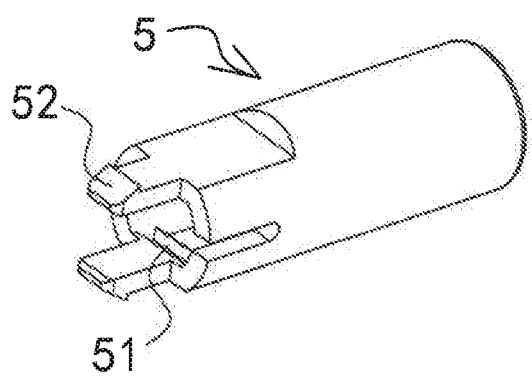
FIG. 8 is the perspective view of the trigger tube in the embodiment of present invention.
Figure 9:
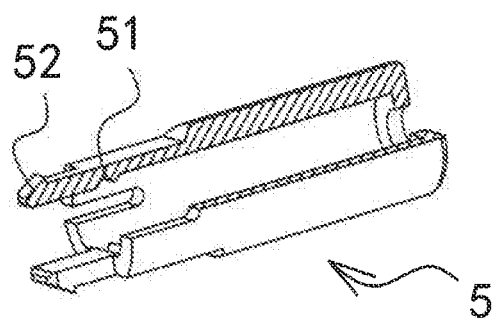
FIG. 9 is the perspective view of the trigger tube with local view in the embodiment of present invention.

The trigger tube 5 is used to protect the injection section of needle body 6 before use (see FIGS. 8 and 9). The main structure of trigger tube 5 is the tubular body and the trigger tube 5 is provided with two inserts 52 extending backward at the rear end and the insert 52 is provided with a barb; the trigger tube 5 is provided with a recess 51 in the tubular body.

8. Spring 7

The spring 7 is used to push the front casing 4 and tail cover 1.

The following is the description of the movement and positioning relationship of trigger tube 5, front casing 4, tail cover 1 and needle base 2 in the main cover 3:

1. Structure Feature

A third positioning structure formed by a concavo-convex structure is provided between the trigger tube 25 and the seat rod 24. That is, a recess 51 is set between the tubular body of trigger tube 5 and seat rod 24 at one side and a convex 22 is set at the other side and the recess 51 contacts the convex 22 to form a third positioning. At the same time, the flexible tenon 41 on the front casing 4 is stuck on the first tenon stage 31 on the main cover 3 to limit the forward movement of front casing 4 relative to the main cover 3.

In summary, this structure resolves reliability issue of trigger tube 5 and front casing 4 protecting the injection section of needle body 6 before and during the use ensures the effective protection of safety of injection section of needle body 6 by the trigger tube 5 and front casing 4 before and during the use.

2. Connection Relationship Feature

The sliding positioning connection is designed to fix the needle base 2 of needle body 6 and the main cover 3. That is, the outer edge of the seat plate 23 of needle base 2 matches with the inner edge of the main cover 3, and the outer edge of corresponding seat plate 23 has a first positioning position and a second positioning position on the inner edge of main cover 3 in the axial direction; during the installation of injection needle to the insulin pen, it uses the axial thrust of tail cover 1 to the needle base 2 to push the seat plate 23 in the main cover 3 to move from the first positioning position to the second positioning position in the axial direction to form the sliding positioning connection relationship between the needle base 2 and main cover 3.

The outer edge of seat plate 23 in the first positioning position matches with inner edge of main cover 3 through the first positioning structure and the outer edge of seat plate 23 in the second positioning position matches with inner edge of main cover 3 through the second positioning structure The first positioning structure is the concavo-convex positioning structure and the concavo-convex positioning structure is formed by a groove 21 provided in the circumferential direction of the outer edge of seat plate 23 and a protruding rib 33 provided on the inner edge of the main cover 3. The second positioning structure is the locking positioning structure and the locking positioning structure is formed by the outer edge and front and rear of seat plate 23 and the slot 34 at the inner edge of main cover 3.

In summary, the purpose of this connection relationship is to use the axial thrust of tail cover to the needle base 2 to push the seat plate 23 on the needle base 2 to move from the first positioning position to the second positioning position to correlate the information of installation of injection needle with the sliding position of seat plate 23 of needle base 2 in the main cover 3 during the installation of injection needle. At the same time, it uses the movement of tail cover 1 to trigger the disconnection of front casing 4.

3. Position Relationship Feature

Establish the corresponding position relationship between the third positioning position and first positioning position. When the trigger tube 5 is located in the third positioning position relative to seat rod 24, the seat plate 23 on the needle base 2 is located in the first positioning position relative to the main cover 3; when the seat plate 23 moves forward from the first positioning position to the second positioning position in the main cover 3 along the axial direction, the trigger tube 5 and the seat rod 24 release the third positioning and forms the sliding connection.

In short, this position relationship feature correlates the information of installation of injection needle with the movement of seat plate in the main cover and unlocking of trigger tube and front casing after the positioning and the correlation of unlocking of trigger tube and front casing after the positioning with the ready injection state of insulin pen and injection needle greatly improve the safety and convenience of injection needle.

Figure 14:
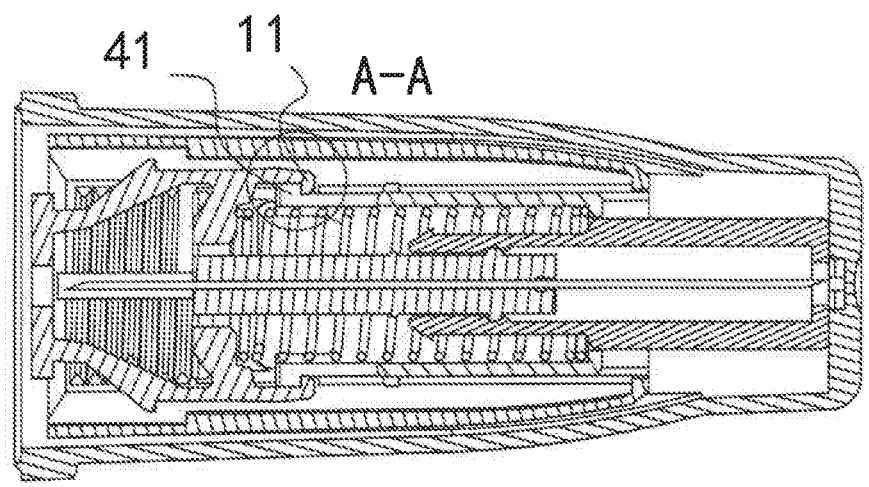
FIG. 14 is the A-A cross sectional view before use in the embodiment of the present invention.
Figure 15:
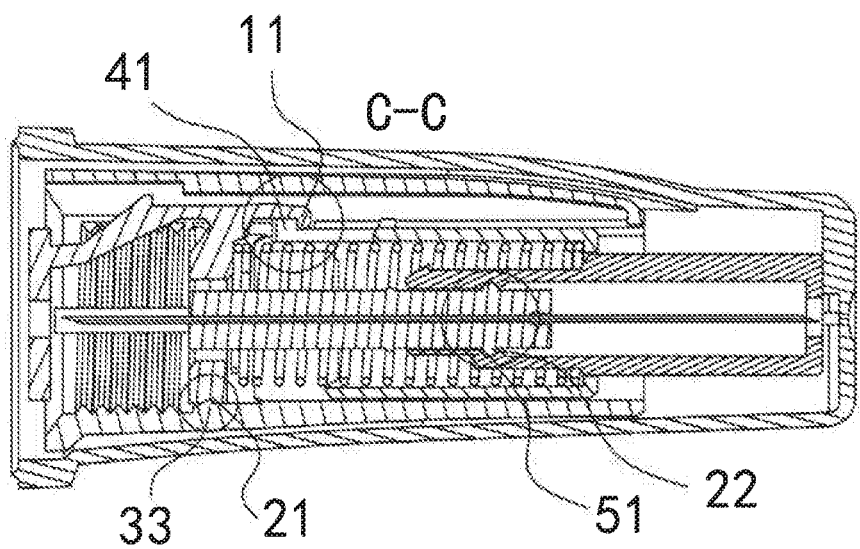
FIG. 15 is the C-C cross sectional view before use in the embodiment of the present invention.
Figure 16:
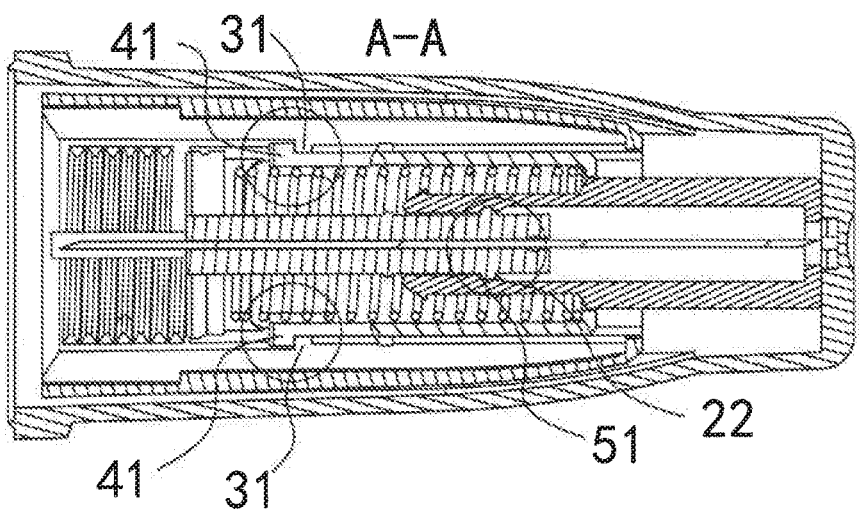
FIG. 16 is the A-A cross sectional view before use removing the tail cover in the embodiment of the present invention.

The following is the description of the connection relationship and position relationship among the components under the assembly state before use of insulin pen needle of this embodiment:

As shown in FIG. 14-16, under the assembly state before use, the outer sheath 8 is installed at the outside of main cover 3, the block 81 of outer sheath 8 is stuck in the bayonet 38 of main cover 3 and extends into the main cover 3 to form the locking connection of outer sheath 8 and main cover 3; the needle base 2 and needle body 6 are located in the main cover 3, the seat plate 23 on the needle base 2 is located in the first positioning position in the main cover 3, and the groove 21 provided in the circumferential direction of the outer edge of seat plate 23 in the first positioning position and the protruding rib 33 provided on the inner edge of the main cover 3 form the concavo-convex positioning structure (see FIG. 15); the tail cover 1 is located in the rear end of main cover 3, the cap 15 on the tail cover 1 is located in the back of seat plate 23 to protect the connecting section of needle body 6 (see FIGS. 14 and 15) and the two front legs 16 on the tail cover 1 extends through the two dodging slots 25 of the seat plate 23 to the front (see FIGS. 14 and 15); the front casing 4 is located in the main cover 3, and the flexible tenon 41 of the front casing 4 is in the first tenon stage 31 of main cover 3 to limit the forward movement of front casing 4 in relative to the main cover 3 (see FIG. 16) and the foot hooks 11 of two front legs 16 of the tail cover 1 hook the flexible tenon 41 of front casing 4 (see FIG. 14); the trigger tube 5 is located in the front end of main cover 3 and extends out of the front end to protect the injection section of needle body 6 (see FIG. 14) and the rear part of trigger tube 5 is installed on the seat rod 24 of needle base 2 and the rear part of trigger tube 5 is located in the front casing 4, and the front end of trigger tube 5 is close to or abutted against the front inner end face of the outer sheath 8, and the recess 51 is stuck in the convex 22 of seat rod 24 to form the positioning (see FIGS. 15 and 16); the spring 7 is against the stopper 13 of two front legs 16 of tail cover 1 at one end and against the inner end face 44 of front casing 4 at the other end (see FIG. 14).

Figure 17:
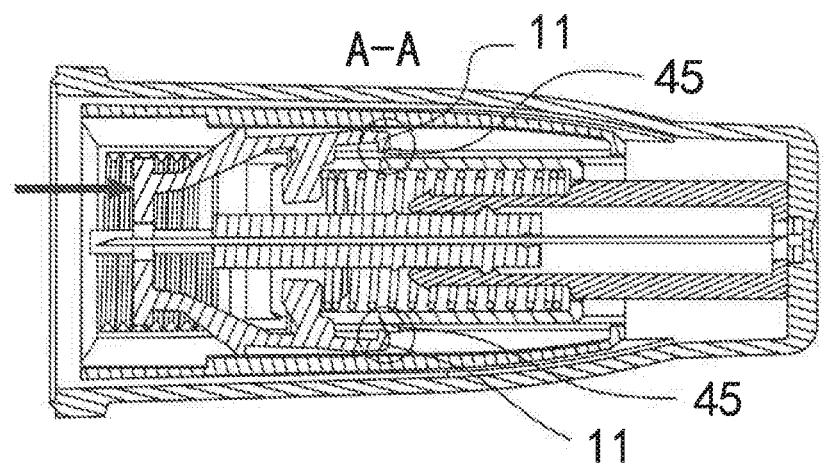
FIG. 17 is the A-A cross sectional view of screwing the insulin pen to the injection needle in the first stage in the embodiment of the present invention.

The operation procedure of insulin injection needle in this embodiment is described as follows:

First Stage:

FIG. 17 shows the state of first stage. From FIG. 17, it's known that under this state, the user screws the insulin pen head to the injection needle of this embodiment. The insulin pen head pushes the tail cover 1 to move forward, and the arrow in FIG. 17 means the thrust generated by the insulin pen head and at the same time, the foot hook 11 of tail cover 1 is lifted by the bevel of convex 42 of front casing 4.

Figure 18:
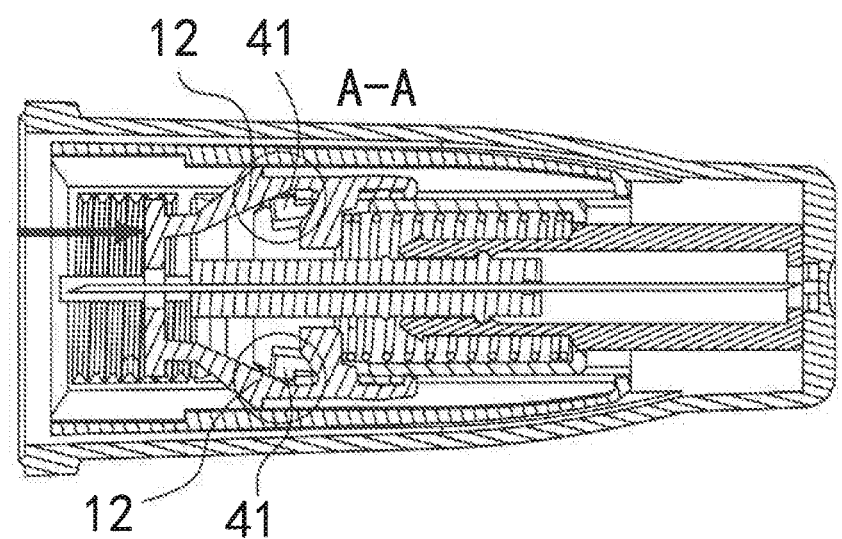
FIG. 18 is the A-A cross sectional view of screwing the insulin pen to the injection needle in the second stage in the embodiment of the present invention.

Second Stage:

FIG. 18 shows the state of second stage. From FIG. 18, it's known that under such state, the insulin pen continues to screw in the injection needle, and the foot hook 11 of tail cover 1 crosses the convex 42 of front casing 4 and at the same time, the bevel 12 of tail cover 1 forces the flexible tenon 41 of front casing 4 bend inward.

Figure 19:
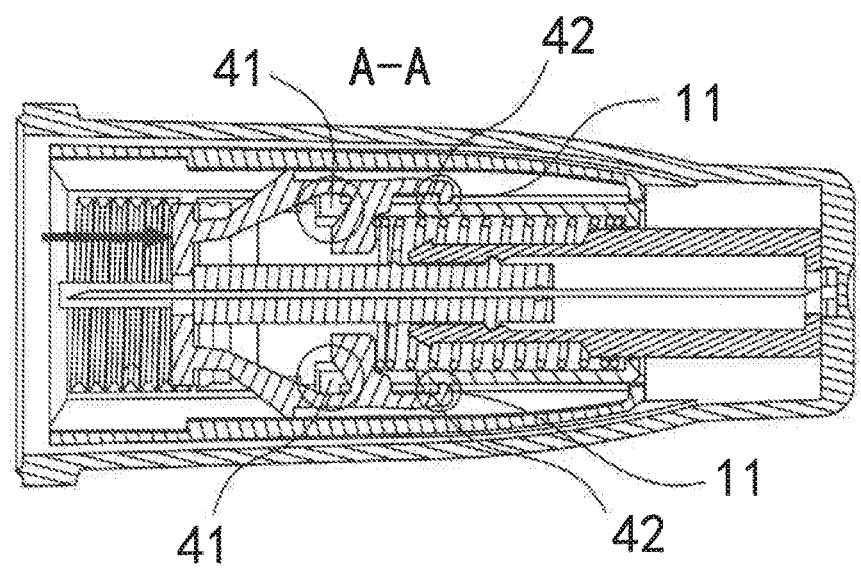
FIG. 19 is the A-A cross sectional view of screwing the insulin pen to the injection needle in the third stage in the embodiment of the present invention.
Figure 20:
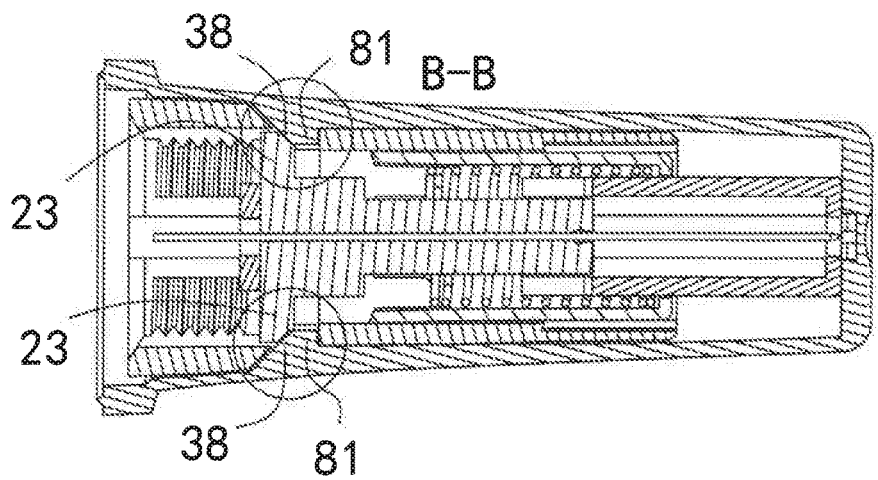
FIG. 20 is the B-B cross sectional view of screwing the insulin pen to the injection needle in the third stage in the embodiment of the present invention.

Third Stage:

FIGS. 19 and 20 show the state of third stage. Under such state, the insulin pen continues to screw in the injection needle and the flexible tenon 41 continues to bend inward, finally forcing the flexible tenon 41 to disconnect from the first tenon stage 31 and fall in the dodging slot 32 and releasing the limit of forward movement of front casing 4 in the main cover 3, and at the same time, front casing 4 moves forward by the push of spring 7 until it stops moving by the convex 42 stopped by the foot hook 11 and limits the forward movement of front casing 4 (see FIG. 19). From FIG. 20, it's known that under such state, the block 81 of outer sheath 8 is stuck in the bayonet 38 of main cover 3 and extends into the main cover 3, and the seat plate 23 of needle base 2 is still located in the first positioning position while the tail cover 1 gradually contacts the seat plate 23 of needle base 2.

Figure 21:
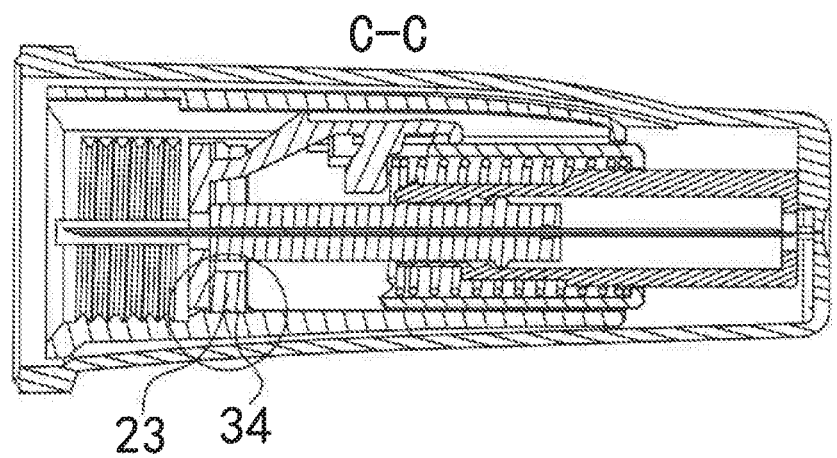
FIG. 21 is the C-C cross sectional view of screwing the insulin pen to the injection needle in the fourth stage in the embodiment of the present invention.
Figure 22:
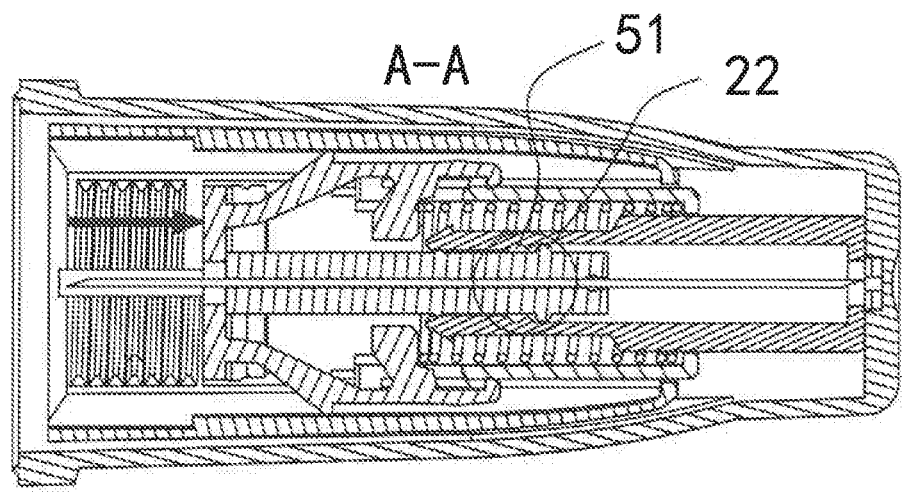
FIG. 22 is the A-A cross sectional view of screwing the insulin pen to the injection needle in the fourth stage in the embodiment of the present invention.
Figure 23:
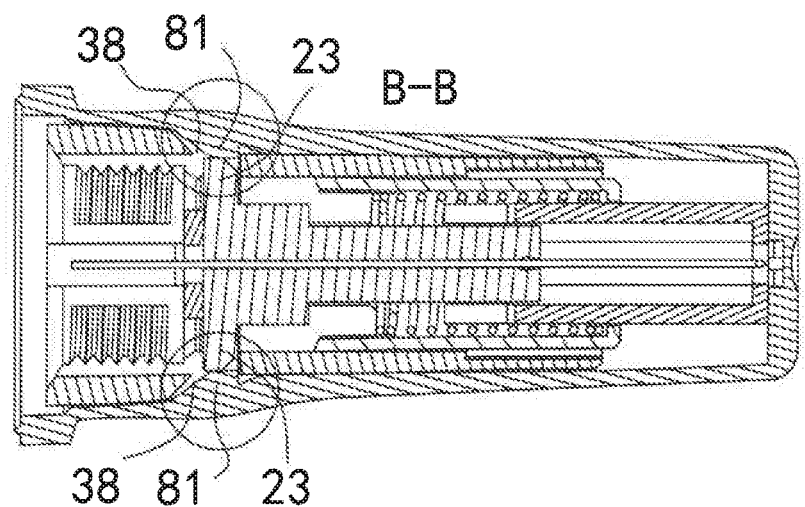
FIG. 23 is the B-B cross sectional view of screwing the insulin pen to the injection needle in the fourth stage in the embodiment of the present invention.
Figure 24:
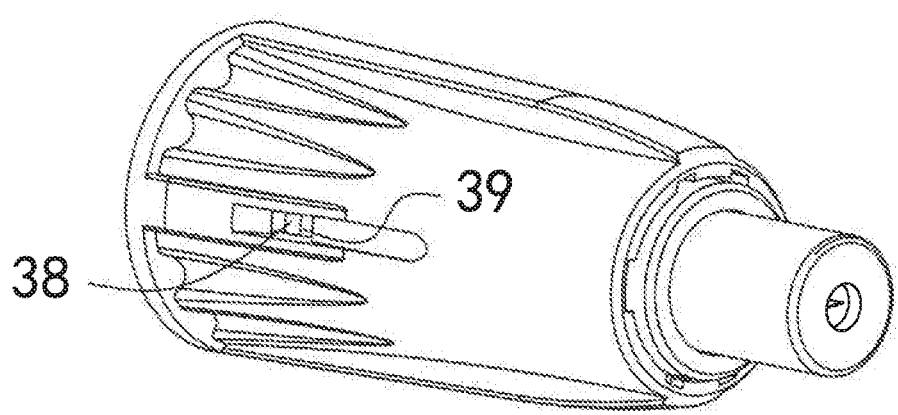
FIG. 24 is the perspective view of fifth stage of using the embodiment of present invention removing the outer sheath.

Fourth Stage:

FIGS. 21, 22 and 23 show the state of Fourth stage. Under such state, the insulin pen continues to screw in the injection needle, the cap 15 of tail cover 1 is against the seat plate 23 of needle base 2 and pushes the seat plate 23 forward from first positioning position to second positioning position (see FIG. 21), and the matching of outer edge and front and rear of seat plate 23 in the second positioning position and the slot 34 at the inner edge of main cover 3 forms the locking positioning structure, and the seat plate 23 is locked in the second positioning position, which could not move forward or backward. Under such state, as the front end of trigger tube 5 is against the inner end face of outer sheath 8, when the needle base 2 moves forward, the positioning of convex 2 of needle base 2 and recess 51 of trigger tube 5 is unlocked (see FIG. 22). Under such state, the outer edge of seat plate 23 lifts the block 81 of outer sheath 8 to disconnect the block 81 and bayonet 38 to cause the unlocking of outer sheath 8 and main cover 3, and it's allowed to remove the outer sheath 8 under such state (see FIG. 23).

Figure 25:
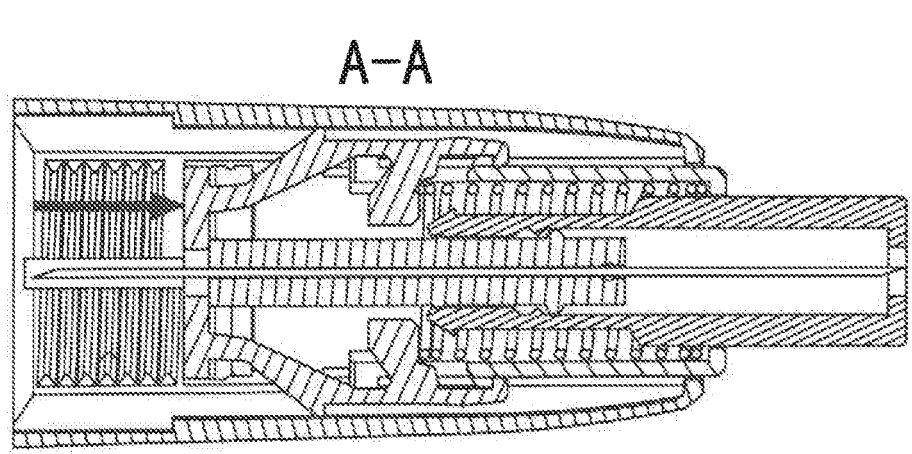
FIG. 25 is the A-A cross sectional view of fifth stage of using the embodiment of present invention removing the outer sheath.
Figure 26:
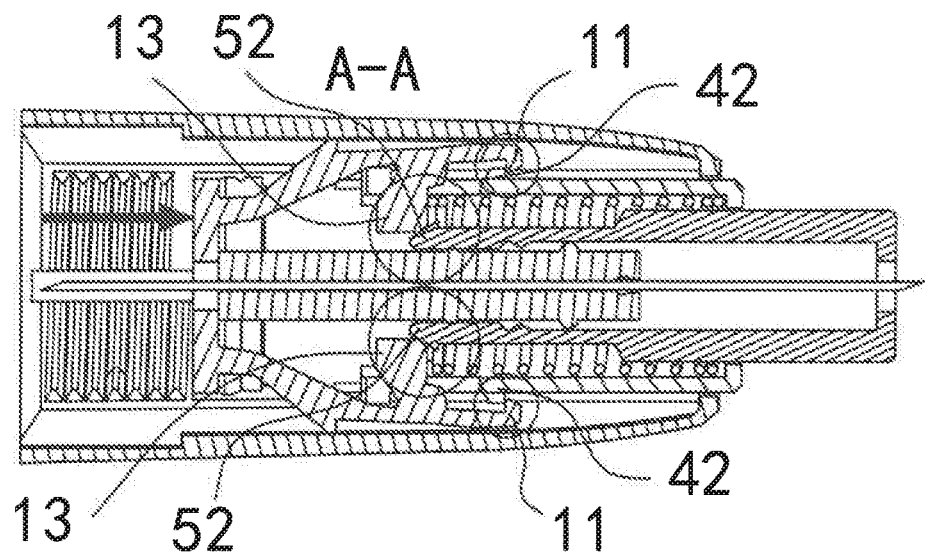
FIG. 26 is the A-A cross sectional view of sixth stage of using the embodiment of present invention with needle starting to penetrate the skin.

Fifth Stage:

FIGS. 25 and 26 show the state of fifth stage. Under such state, remove the outer sheath 8 manually.

Sixth Stage:

FIG. 26 shows the state of sixth stage. Under such state, the trigger tube 5 contacts the human skin and the needle body 6 starts to penetrate into the human skin. When the front end of trigger tube 5 contacts the human skin, the trigger tube 5 moves backward and at the same time, the insert 52 of trigger tube 5 lifts the stopper 13 on the tail cover 1, forcing the foot hook 11 of tail cover 1 to gradually disconnect from the convex 42 of front casing 4.

Figure 27:
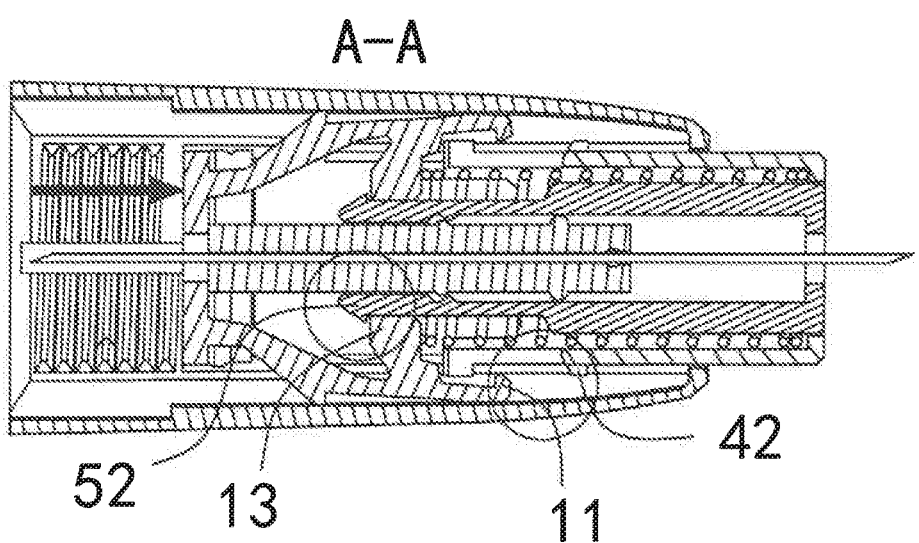
FIG. 27 is the A-A cross sectional view of seventh stage of using the embodiment of present invention with needle penetrating the skin.

Seventh Stage:

FIG. 27 shows the state of seventh stage. Under such state, the trigger tube 5 continues to move backward until the foot hook 11 completely disconnect from the convex 11 and then the front casing 4 moves forward by the spring 7 and extends out of the front end of main cover 3 and the front end of front casing 4 is blocked by the human skin and moves together with the front end of trigger tube.

Figure 28:
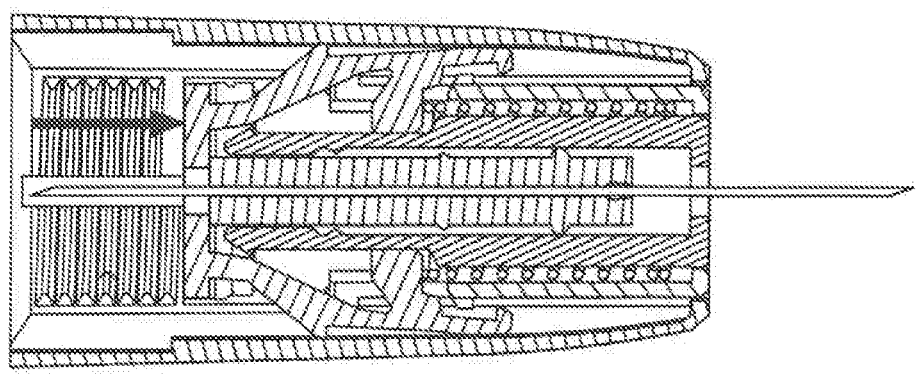
FIG. 28 is the A-A cross sectional view of eighth stage of using the embodiment of present invention with needle completely penetrating the skin and injecting the insulin.

Eighth Stage:

FIG. 28 shows the state of eighth stage. Under such state, the needle body 6 completely penetrates into the human skin and starts injecting the insulin.

Figure 29:
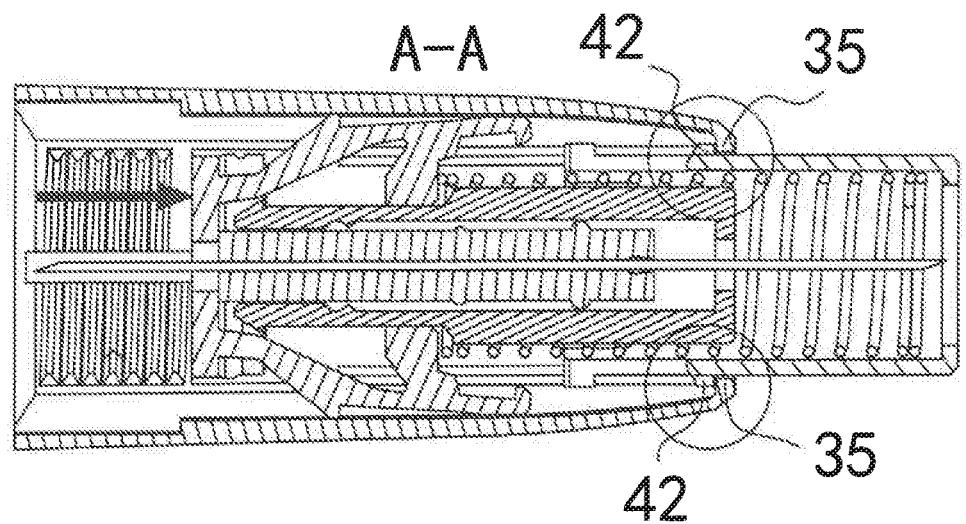
FIG. 29 is the A-A cross sectional view of ninth stage of using the embodiment of present invention finishing injecting the insulin and pulling out of the skin.
Figure 30:
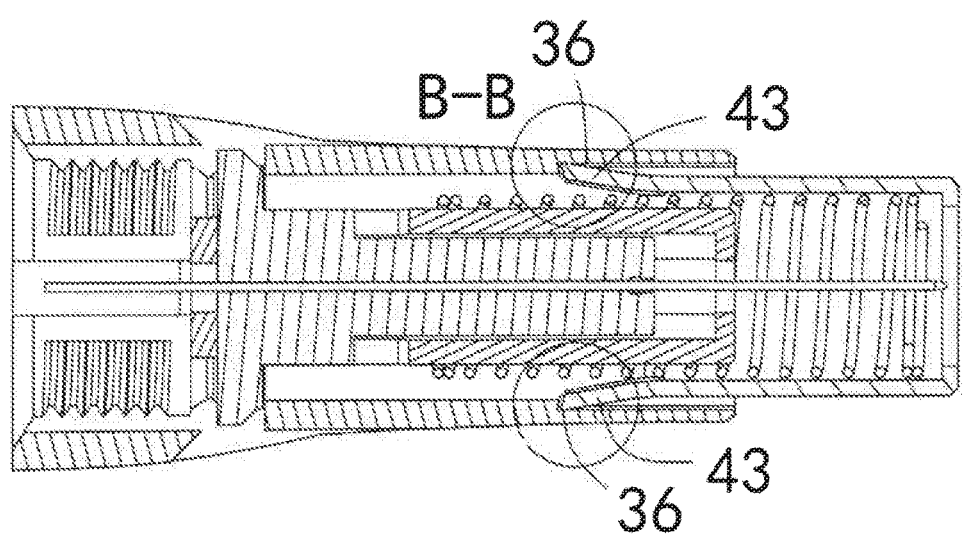
FIG. 30 is the B-B cross sectional view of ninth stage of using the embodiment of present invention finishing injecting the insulin and pulling out of the skin.

Ninth Stage:

FIGS. 29 and 30 show the state of ninth stage. Under such state, the injection needle is pulled out from the skin, and the front casing 4 is pushed out of the front end of main cover 3 by the spring 7 until the convex 42 of front casing 4 is stopped by the second tenon stage 35 on the main cover 3, and at this time, the front casing 4 is used to protect the injection section of needle body 6; At the same time, the flexible tail fin 43 of front casing 4 expands and is stuck in the anti-back slot 36 of main cover 3 to form the limit for the backward movement of front casing 4 to prevent the returning of front casing 4 (see FIG. 30).

Figure 31:
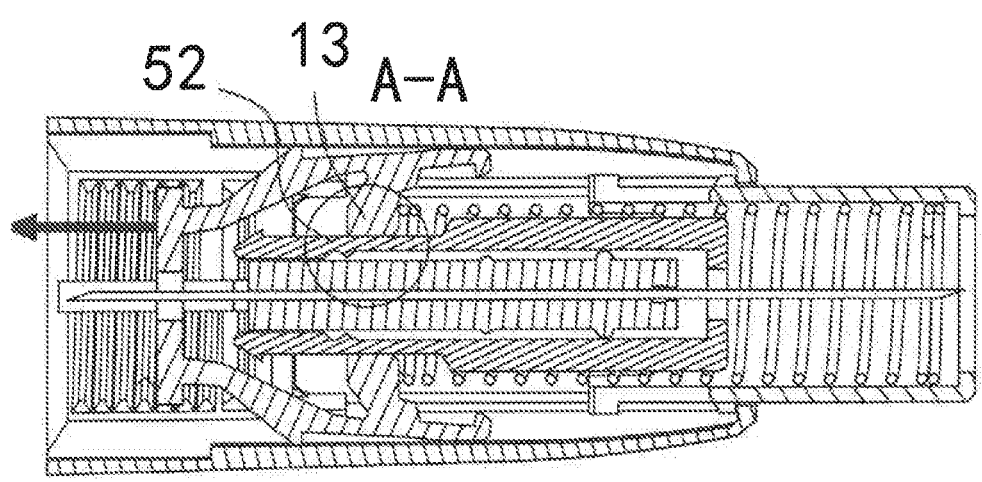
FIG. 31 is the A-A cross sectional view of screwing the insulin pen out of the injection needle in the tenth stage in the embodiment of the present invention.

Tenth Stage:

FIG. 31 shows the state of tenth stage. Under such state, the insulin pen is removed from the injection needle, the tail cover 1 moves backward by the spring 7 and the two stoppers 13 on the tail cover 1 hold the inserts 52 of trigger tube 5 to move the trigger tube 5 backward.

Figure 32:
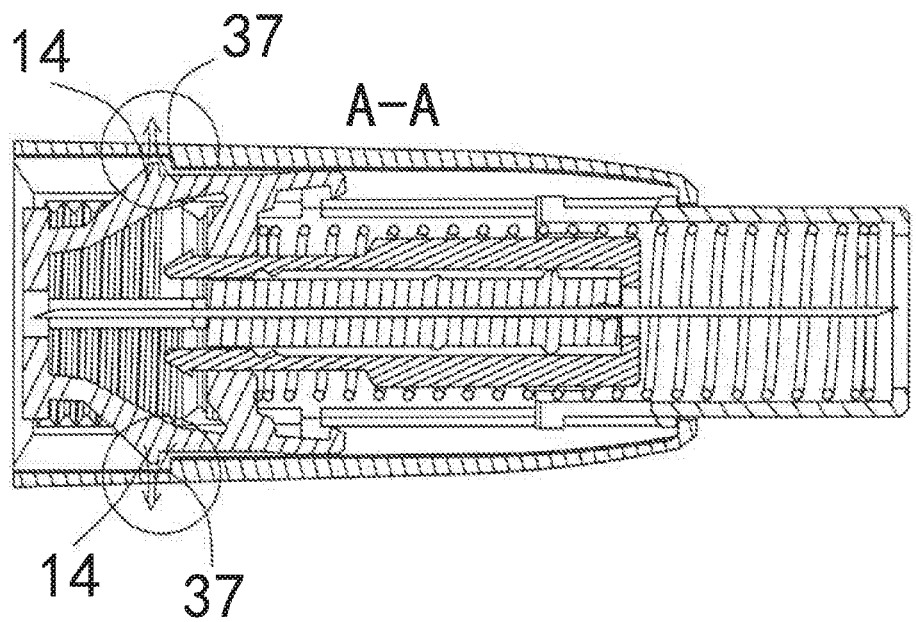
FIG. 32 is the A-A cross sectional view after use in the embodiment of the present invention.

State after Use:

FIG. 32 shows the state after use. Under such state, the insulin pen is screwed out, the trigger tube 5 continues to move backward until the front end of seat rod 24 on the needle base 2 contacts the inner end face of trigger tube 5 to stop. Then the sharp tenon 14 on the tail cover 1 falls in the third tenon stage 37 of main cover 3 to form the limit for forward movement of tail cover 1, and the barbs of inserts 52 of trigger tube 5 match the stoppers to limit the backward movement of tail cover 1 in the back of main cover 3, and at this time, the tail cover 1 is used to protect the connecting section of needle body 6 and prevent the repeated use of injection needle.

From the above embodiment, it's known that the matching and function relationship among the components of insulin injection needle of present invention is as following:

1. The relationship before use is as follows:

(1) The matching of block 81 of outer sheath 8 and bayonet 38 of main cover 3 is used for the locking of outer sheath 8 and main cover 3;

(2) The matching of groove 21 of needle base 2 and protruding rib 33 of main cover 3 is used for the positioning of needle base 2 and main cover 3 (first positioning);

(3) The matching of convex 22 of needle base 2 and recess 51 of trigger tube 5 is used for positioning of trigger tube 5 and needle base 2;

(4) The matching of flexible tenon 41 of front casing 4 and first tenon stage 31 of main cover 3 is used to limit the forward movement of front casing 4 in the main cover 3;

(5) The matching of flexible tenon 41 of front casing 4 and foot hook 11 of tail cover 1 is used to limit the backward movement of tail cover 1 in relative to front casing 4;

(6) The matching of spring 7, stopper 13 of tail cover 1 and inner end face 44 of front casing 4, wherein one end of spring 7 is against the stopper 13 of tail cover 1 and the other end is against the inner end face 44 of front casing 4, is used for the connection and positioning of tail cover 1, front casing 4 and spring 7.

2. The Relationship During Use is as Follows:

(1) The matching of bevel 12 of tail cover 1 and flexible tenon 41 of front casing 4 is used to release the limit for the forward movement of front casing 4 in the main cover 3. Specifically: during the use, along the forward movement of tail cover 1, the bevel 12 presses the flexible tenon 41 to bend inward to finally force the flexible tenon 41 to unhook from the first tenon stage 31 to release the limit of forward movement of front casing 4 in the main cover 3;

(2) The matching of foot hook 11 of tail cover 1 and convex 42 of front casing 4 is used to limit the forward movement of front casing 4. Specifically: during the use, along the screwing of insulin pen to the injection needle, the tail cover 1 moves forward, the foot hook 11 is lifted by the bevel of convex 42 and crosses the convex 42, and after the disconnection of flexible tenon 41 from first tenon stage 31, the foot hook 11 hooks the convex 42 to limit the forward movement of front casing 4 (the convex 42 is stopped by the foot hook 11 during the forward movement);

(3) The matching of seat plate 23 of needle base 2 and slot 34 of main cover 3 is used for the positioning of needle base 2 and main cover 3 (second positioning);

(4) The matching of flexible tenon 41 of front casing 4 and dodging slot 32 of main cover 3 is used to avoid the interference of flexible tenon 41 to the spring 7. Specifically: during the use, the flexible tenon 41 crosses the first tenon stage 31 of main cover 3 and falls in the dodging slot 32 to avoid the interference of flexible tenon 41 to the spring 7 (avoid the flexible tenon 41 from touching spring 7 to form the interference);

(5) The matching of cap 15 of tail cover 1 and seat plate 23 of needle base 2 to realize the moving positioning. Specifically: during the use, along the forward movement of tail cover 1, the cap 15 gradually touch the seat plate 23 and push the seat plate 23 to disconnect from the first positioning and move forward until it falls in the second positioning and could not be moved;

(6) The matching of seat plate 23 of needle base 2, block 81 of outer sheath 8 and bayonet 38 of main cover 3 is to correlate the readiness of removing the outer sheath 8 with the readiness of insulin pen and injection needle. Specifically: during the use, when the seat plate 23 of needle base 2 falls in the slot 34 of main cover 3, firstly it shows that the injection needle is formally installed on the head of insulin pen; secondly, the outer edge of seat plate 23 lifts the block 81 of outer sheath 8 to deform the outer sheath 8 and finally causes the block 81 of outer sheath 8 to disconnect from the bayonet 38 of main cover 3 to realize the unlocking of outer sheath 8 and main cover 3 to remove the outer sheath 8; thirdly, as the front end of trigger tube 5 is against the inner end face of outer sheath 8, when the needle base 2 moves forward, the positioning between the convex 22 of needle base 2 and the recess 51 of trigger tube 5 is released to show the trigger tube 5 is ready to be triggered.

(7) The matching of insert 52 of trigger tube 5 and stopper 13 of tail cover 1 is used to release the limit for forward movement of front casing 4. Specifically: when the front end of trigger tube 5 contacts the human skin, the trigger tube 5 moves backward and at the same time, the insert 52 of trigger tube 5 lifts the stopper 13 on the tail cover 1, forcing the foot hook 11 of tail cover 1 to gradually disconnect from the convex 42 of front casing 4, and after the complete disconnection, the front casing 4 moves forward by the spring 7 and extends out of the main cover 3, and the front end of front casing 4 is blocked by the skin of human body and moves together with the front end of trigger tube 5 until the needle is penetrated into the skin to inject the insulin.

3. The Relationship after Use is as Follows:

(1) The matching of convex 42 of front casing 4 and second tenon stage 35 of main cover 3 is used to limit the outward extension of front casing 4 from the main cover 3 (to prevent the front casing 4 from sliding out of the main cover 3);

(2) The matching of flexible tail fin 43 of front casing 4 and anti-back slot 36 of main cover 3 is used to limit the inward returning of front casing 4 from the main cover 3 (to prevent the front casing 4 from returning from the main cover 3);

(3) The matching of sharp tenon 14 of tail cover 1 and third tenon stage 37 of main cover 3 is used to prevent the tail cover 1 from moving forward in the main cover 3 under the external force and prevent the repeated use.

Embodiment 2: Insulin Pen Needle with Front End Needle Tip Protection

Figure 36:
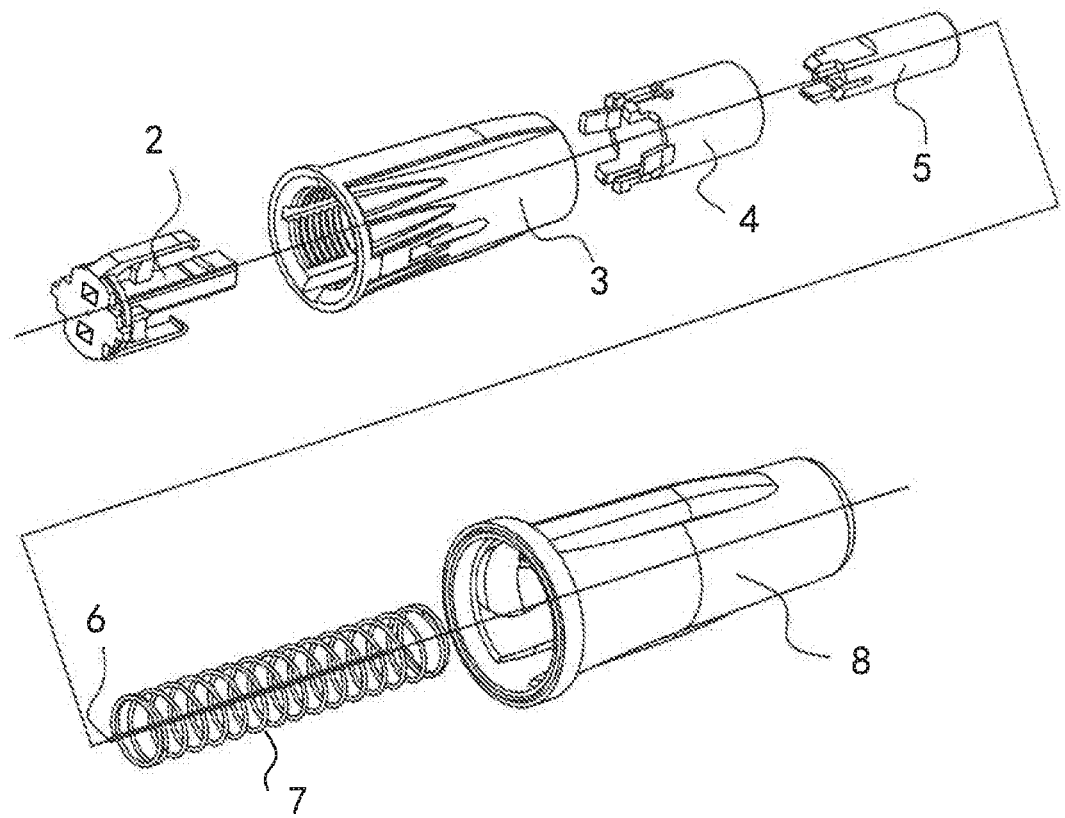
FIG. 36 is the exploded view of the insulin pen needle in another embodiment of present invention.

As shown in FIG. 36, the injection needle consists of a needle body 6, needle base 2, main cover 3, outer sheath 8, front casing 4, trigger tube 5 and spring 7.

Figure 37:
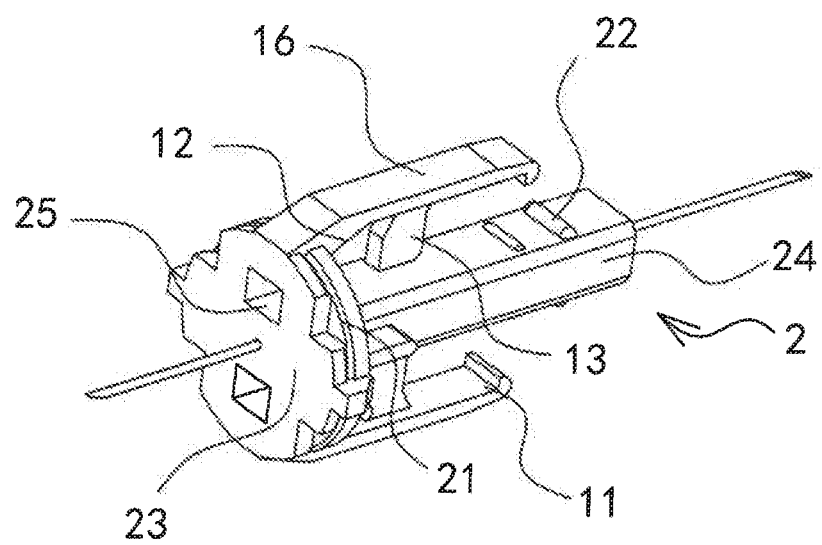
FIG. 37 is the exploded view of the needle base in another embodiment of present invention.

After the complete understanding of insulin pen needle in embodiment 1, the embodiment 2 only has the front end needle tip protection structure in comparison with embodiment 1 and it doesn't have the rear end needle tip protection structure. Specifically, the structure design has the following differences:

Firstly, the embodiment 2 eliminates the tail cover 1 in the embodiment 1;

Secondly, the embodiment 2 replants the two front legs of tail cover 1 in the embodiment 1 to the needle base 2 in embodiment 1 as shown in FIG. 37. Embodiment 2 keeps the stopper 13 and foot hook 11 in the front leg 16. Embodiment 2 eliminates the sharp tenon 14 in the front leg 16.

Thirdly, as the embodiment 2 eliminates the sharp tenon 14 in the front leg 16, it eliminates the third tenon stage 37 at the inner wall of main cover 3.

Fourthly, comparing the embodiment 2 with embodiment 1, the position of front leg 16 changes under the assembly state before use (it's in the more frontal position than the original position, and it passes over the convex 42 of front casing 4), so it eliminates the bevel 45 at the side of convex 42.

The other structures of insulin pen needle of embodiment 2 is completely the same as that in embodiment 1 and it's not described repeatedly to save space and it's easy for those skilled in the art to easily understand the embodiment 2 after the full understanding of embodiment 1.

Figure 38:
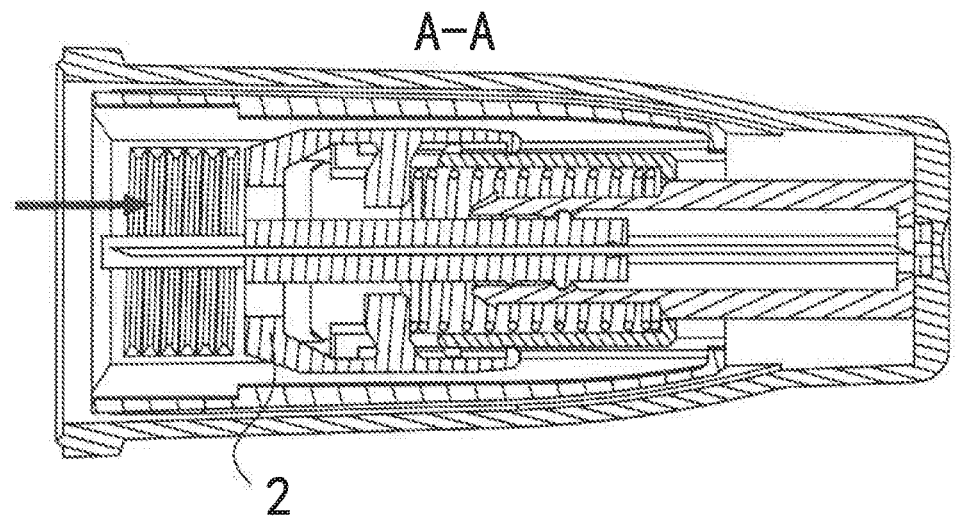
FIG. 38 is the A-A cross sectional view before use in another embodiment of the present invention.
Figure 39:
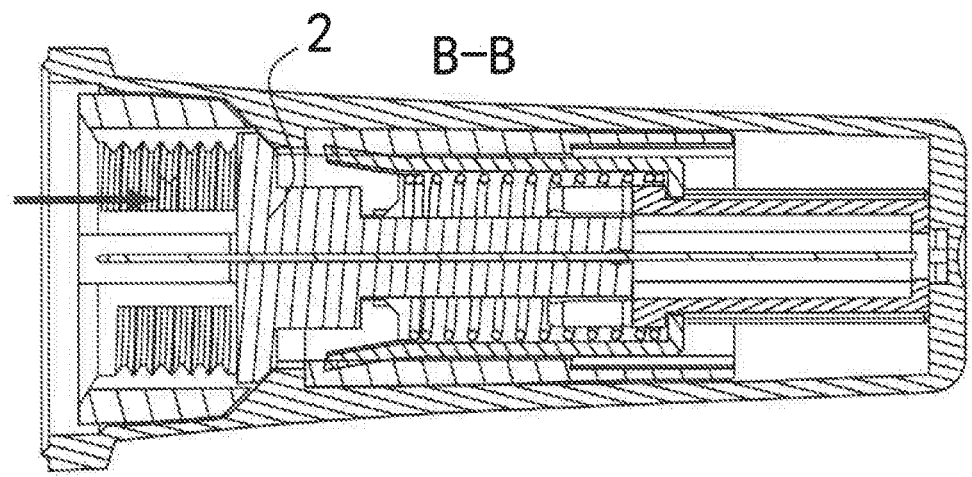
FIG. 39 is the B-B cross sectional view before use in another embodiment of the present invention.

The operation procedure of insulin injection needle in the embodiment 2 is described as follows:

As shown in FIGS. 38 and 39, under the assembly state before use, the outer sheath 8 is installed at the outside of main cover 3, the block 81 of outer sheath 8 is stuck in the bayonet 38 of main cover 3 and extends into the main cover 3 to form the locking connection of outer sheath 8 and main cover 3; the needle base 2 and needle body 6 are located in the main cover 3, the seat plate 23 on the needle base 2 is located in the first positioning position in the main cover 3, and the groove 21 provided in the circumferential direction of the outer edge of seat plate 23 in the first positioning position and the protruding rib 33 provided on the inner edge of the main cover 3 form the concavo-convex positioning structure and the two front legs 16 on the seat plate 23 extends to the front; the front casing 4 is located in the main cover 3, and the flexible tenon 41 of the front casing 4 is in the first tenon stage 31 of main cover 3 to limit the forward movement of front casing 4 in relative to the main cover 3; the trigger tube 5 is located in the front end of main cover 3 and extends out of the front end to protect the injection section of needle body 6, and the trigger tube 5 is provided with the limit for the forward movement in relative to main cover 3, and the rear part of trigger tube 5 is installed on the seat rod 24 of needle base 2 and the rear part of trigger tube 5 is located in the front casing 4, the trigger tube 5 is located in the third positioning position and the front end of trigger tube 5 is close to or abutted against the front inner end face of the outer sheath 8, and the recess 51 is stuck in the convex 22 of seat rod 24 to form the positioning and at this time, the seat plate 23 on the needle base 5 is located in the first positioning position in relative to the main cover 3; the spring 7 is against the stopper 13 of two front legs 16 of needle base 2 at one end and against the inner end face 44 of front casing 4 at the other end.

Figure 40:
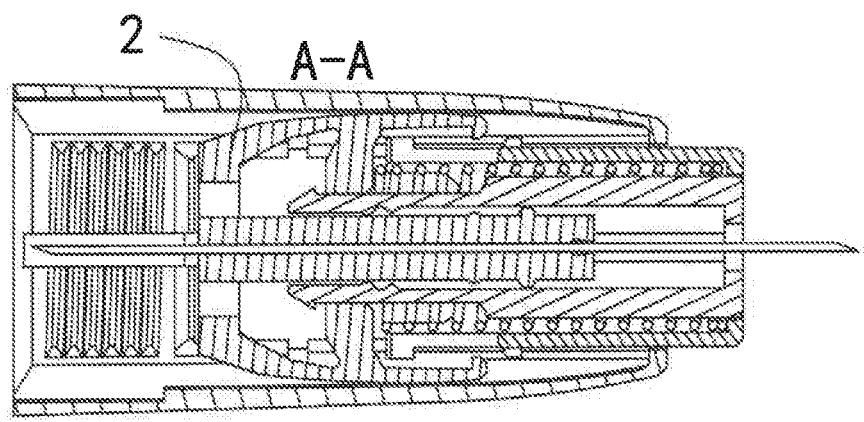
FIG. 40 is the A-A cross sectional view of using another embodiment of present invention removing the outer sheath.
Figure 41:
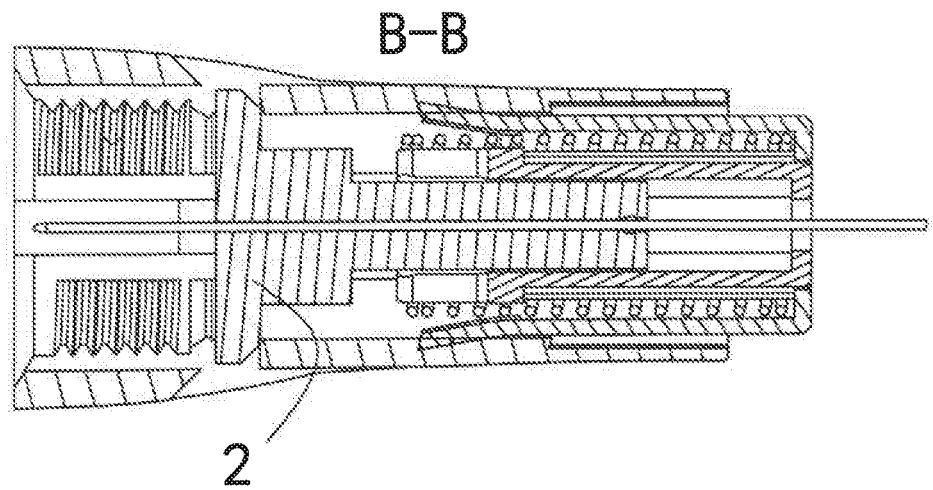
FIG. 41 is the B-B cross sectional view of using another embodiment of present invention removing the outer sheath.

As shown in FIGS. 40 and 41, when the user screws the head of insulin pen to the injection needle of this embodiment, the head of insulin pen pushes the seat plate 23 to move forward, and the bevel 12 of inner side of front leg 16 presses the flexible tenon 41 to bend inward to finally force the flexible tenon 41 to unhook from the first tenon stage 31 and fall in the dodging slot 32 to release the limit of forward movement of front casing 4 in the main cover 3 and at the same time, the front casing 4 is moved forward by the spring 7 until the convex 42 is stopped by the foot hook 11 to limit the forward movement of front casing 4; at the same time, the seat plate 23 moves forward from the first positioning position to the second positioning position, and the matching of outer edge and front and rear of seat plate 23 in the second positioning position and the slot 34 at the inner edge of main cover 3 forms the locking positioning structure, and the seat plate 23 is locked in the second positioning position, which could not move forward or backward. Under such state, as the front end of trigger tube 5 is against the inner end face of outer sheath 8, when the needle base 2 moves forward, the third positioning of convex 2 of needle base 2 and recess 51 of trigger tube 5 is unlocked and at this time, the trigger tube 5 and seat rod 24 forms the sliding connection. Under such state, the outer edge of seat plate 23 lifts the block 81 of outer sheath 8 to disconnect the block 81 and bayonet 38 to cause the unlocking of outer sheath 8 and main cover 3, and it's allowed to remove the outer sheath 8 under such state. Next when the front end of trigger tube 5 contacts the human skin, the needle body 6 starts penetrating into the human skin, the trigger tube 5 moves backward and at the same time, the insert 52 of trigger tube 5 lifts the stopper 13 on the front leg 16, forcing the foot hook 11 of front leg 16 to gradually disconnect from the convex 42 of front casing 4, and after the complete disconnection, the front casing 4 moves forward by the spring 7 and extends out of the main cover 3, and the front end of front casing 4 is blocked by the skin of human body and moves together with the front end of trigger tube 5 until the needle is penetrated into the skin to inject the insulin.

Figure 42:
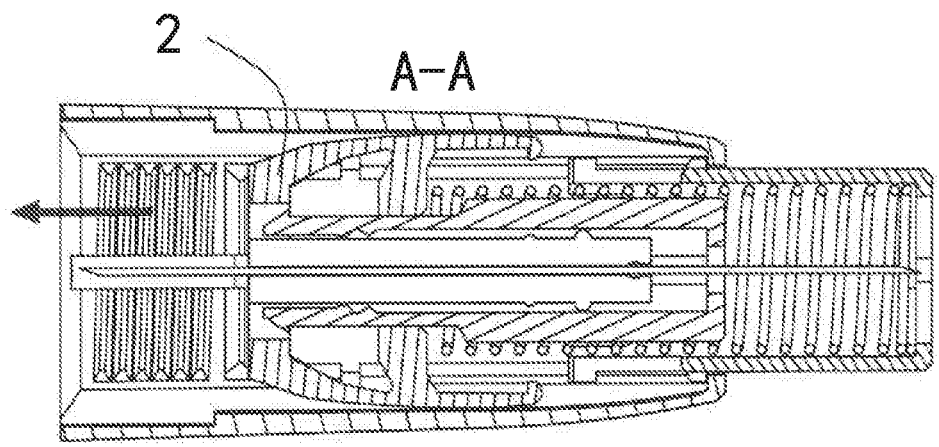
FIG. 42 is the A-A cross sectional view after use in another embodiment of the present invention.
Figure 43:
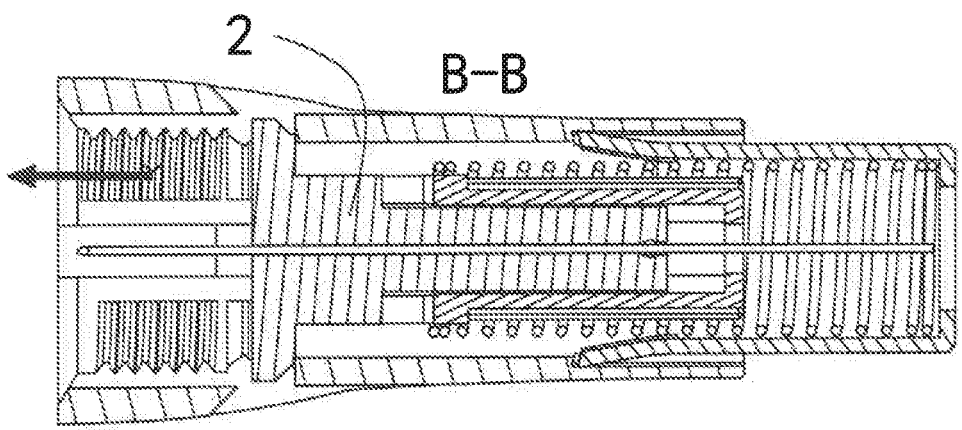
FIG. 43 is the B-B cross sectional view after use in another embodiment of the present invention.

As shown in FIGS. 42 and 43, when the injection needle is pulled out from the skin after the use, the front casing 4 is pushed out of the front end of main cover 3 by the spring 7 until the convex 42 of front casing 4 is stopped by the second tenon stage 35 on the main cover 3, and at this time, the front casing 4 is used to protect the injection section of needle body 6; at the same time, the flexible tail fin 43 of front casing 4 expands and is stuck in the anti-back slot 36 of main cover 3 to form the limit for the backward movement of front casing 4 to prevent the returning of front casing 4, and finally the injection needle is removed from the head of insulin pen.

The content and change of above embodiment is as follows:

1. In the above two embodiments, the first positioning structure is the concavo-convex positioning structure, and it also could be the elastic positioning structure or friction positioning structure to replace it to obtain the same or similar technical result, which could be understood by those skilled in the art. In theory, the first positioning position shall be the non-locking positioning structure, as the outer edge of seat plate 23 and inner edge of main cover 3 before use are in the first positioning position, while the outer edge of seat plate 23 and inner edge of main cover 3 during use require the axial sliding between them.

The elastic positioning structure is formed by matching of an elastic bead pin and a pitting; among the elastic bead pin and pitting, one is set in the outer edge of seat plate 23 and the other is set in the inner edge of main cover 3.

The friction positioning structure is formed by the friction matching of outer edge of seat plate 23 and inner edge of main cover 3.

2. In the above two embodiments, the second positioning structure is the locking positioning structure, and it also could be the elastic positioning structure, friction positioning structure or end face abutment positioning structure to replace it to obtain the same or similar technical result, which could be understood by those skilled in the art. In theory, the second positioning position could be the non-locking positioning structure and the locking positioning structure. The elastic positioning structure, friction positioning structure or end face abutment positioning structure belongs to the non-locking positioning structure, while the locking positioning structure formed by the matching of outer edge and front and rear of seat plate 23 and the slot 34 at the inner edge of main cover 3 belongs to the locking positioning structure. But in this kind of locking positioning structure, when the width of slot 34 is larger than thickness of seat plate 23, there is the gap, and when the gap is large enough to a certain extent, the seat plate 23 can slide back and forth in the slot 34 to change to non-locking positioning structure.

The end face abutment positioning structure is formed by the abutment matching of front end at the outer edge of seat plate 23 and the inner end face at the inner edge of main cover 3.

3. In the above two embodiments, the bayonet 38 is located in the second positioning position in axial direction of main cover 3, actually it could obtain the same or similar technical result is the bayonet 38 is in the second positioning position or position near to second positioning position. The position near to second positioning position means the position a little bit anterior or posterior to the base point of second positioning position. This position relationship in the present invention is to meet the requirement of specific relationship, which is: when the seat plate 23 moves from first positioning position to second positioning position, the outer edge of seat plate 23 lifts the block 81 of outer sheath 8 to deform the outer sheath 8 and finally causes the block 81 of outer sheath 8 to disconnect from the bayonet 38 of main cover 3 to realize the unlocking of outer sheath 8 and main cover 3 to finally correlate the readiness of removing the outer sheath 8 with the readiness of insulin pen and injection needle.

Figure 33:
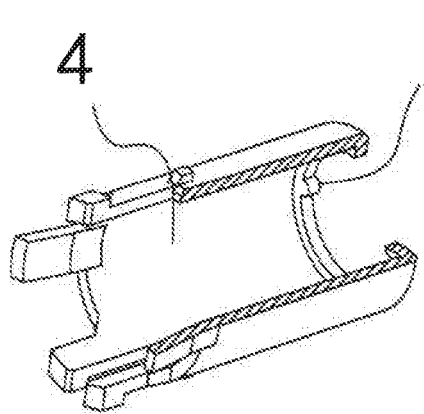
FIG. 33 is the perspective view of the front casing shown as "wedge" in the present invention.
Figure 34:
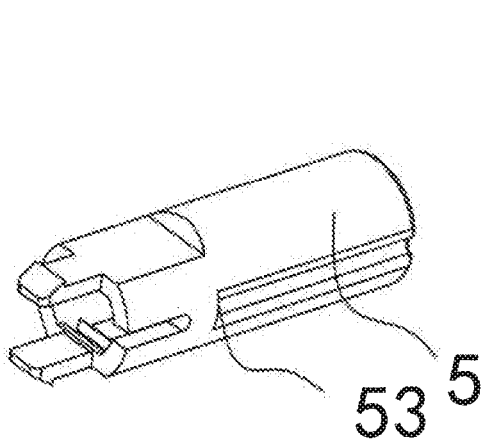
FIG. 34 is the perspective view of the trigger tube shown as "stopper" in the present invention.
Figure 35:
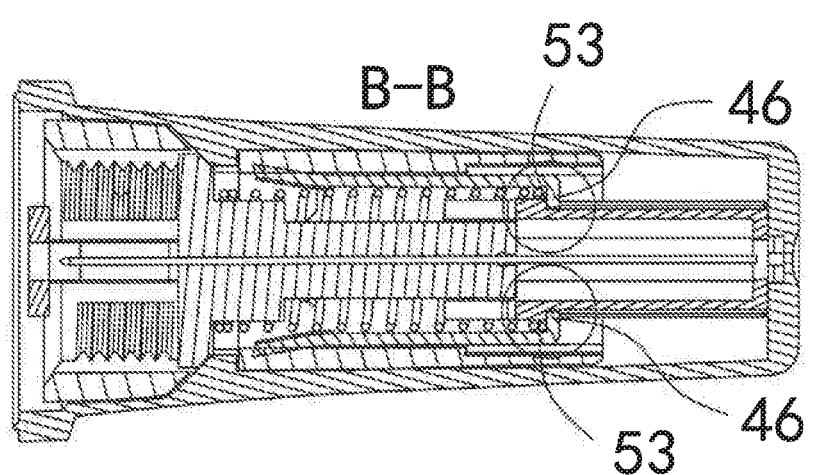
FIG. 35 is the B-B cross sectional view of matching "wedge" and "stopper"

4. In the above two embodiments, the trigger tube 5 is provided with the limit for forward movement in relative to the main cover 3, and the limit is formed by the front end of trigger tube 5 is close to or abutted against the front inner end face of the outer sheath 8. In order to realize the limit for the forward movement of trigger tube 5, the other structures could be applied, as shown in FIG. 33-35, the stopper 53 of trigger tube 5 is abutted against the wedge 46 on the inner end face 44 of front casing 4 to form the limit for forward movement of trigger tube 5 in relative to main cover 3.

5. The above two embodiments are used to describe the technical plan of present invention and from the view of background technology introduction and the technical problems to be solved and invention purpose, it mainly relates to the needle base 2, main cover 3, outer sheath 8, trigger tube 5, front casing 4, spring 7 and the structure and connection relationship among them, and it doesn't relate to the locking structure between outer sheath 8 and main cover 3. In other words, the locking structure between outer sheath 8 and main cover 3 is the unnecessary structure for the present invention, and it's allowed to make changes for them, e.g. It's included in the scope of protection of the present invention whether the locking structure between outer sheath 8 and main cover 3 is available or not. For example, it's included in the scope of protection of the present invention whether the rear end needle tip protection structure is available or not.

It should be noted that the above described embodiments are only for illustration of technical concept and characteristics of present invention with purpose of making those skilled in the art understand the present invention, and thus these embodiments shall not limit the protection range of present invention. The equivalent changes or modifications according to spiritual essence of present invention shall fall in the protection scope of present invention.

The invention claimed is:

1. An insulin injection needle with needle tip protection includes:
    a needle body, the needle body has an injection section extending in a forward direction, a connecting section extending in a rearward direction and a fixing section between the injection section and the connecting section;
    a needle base, the needle base is used to fix the needle body and the fixing section of the needle body is fixed to the needle base, the injection section of the needle body extends from the front end of needle base and the connecting section of needle body extends from the rear end of needle base;
    a main cover, the main cover consists of a cylindrical structure in which the needle base and the needle body are located under assembly state, and the rear end of the main cover is connected to a insulin pen;
wherein:
    the needle base consists of a seat plate and a seat rod, the seat rod is located in the front end of the seat plate and connected with the seat plate in a fixed way; the seat plate is provided with two dodging grooves and the outer edge of the seat plate matches with the inner edge of the main cover, and the outer edge of corresponding seat plate has a first positioning position and a second positioning position on the inner edge of the main cover with spacing in the axial direction; during the installation of the injection needle to the insulin pen, it uses the axial thrust of a head of the insulin pen to the needle base to push the seat plate in the main cover to move from the first positioning position to the second positioning position in the axial direction to form a sliding positioning connection relationship between the needle base and the main cover; the outer edge of the seat plate in the first positioning position matches with the inner edge of the main cover through a first positioning structure, the outer edge of the seat plate in the second positioning position matches with the inner edge of the main cover through a second positioning structure; the first positioning structure is a concavo-convex positioning structure, an elastic positioning structure, or a frictional positioning structure; and the second positioning structure is a concavo-convex positioning structure, an elastic positioning structure, a friction positioning structure, a locking positioning structure or an end face abutment positioning structure;
    the inner wall of the main cover is provided with a first tenon stage in the middle, a second tenon stage in the front end and a third tenon stage in the rear end, and the inner wall of the main cover is provided with a anti-back slot in the forepart; the main cover is provided with a tail cover, a front casing, a trigger tube and a spring;
    the tail cover consists of a cap and two front legs; the cap is an end cap or a ring body and the center of the cap is provided with a needle hole for only inserting the needle body connecting section, the axis of the needle hole is parallel to the axis of the main cover; the two front legs are fixedly attached to the front end of the cap and are arranged symmetrically with reference to the axis of the needle hole, and the inner side of each front leg is provided with a bevel at the root position, a stopper extending inward in the middle and a foot hook in the end position; the outer side of each front leg is provided with a sharp tenon in the middle;
    the main structure of the front casing is the tubular body and the front casing is provided with an inner end face at the inner side of the front end; the front casing is provided with a flexible tenon extending backward and a flexible tail fin extending backward, the flexible tenon and the flexible tail fin are arranged in a staggered way in the circumferential direction of the front casing; the front casing is provided with a convex extending outward at the outer side in the middle, the convex and the flexible tenon are in the corresponding position in the circumferential direction of the front casing, the convex is provided with a bevel at the side of the flexible tenon;
    the main structure of the trigger tube is a tubular body, the trigger tube is provided with two inserts extending backward at the rear end, the insert is provided with a barb; a recess is set between the tubular body of the trigger tube and the seat rod at one side, and a convex is set at the other side, the recess contacts the convex to form a third positioning;
    under the assembly state before use, the seat plate is located in the first positioning position in the main cover, the tail cover is located in the rear end of the main cover, the cap on the tail cover is located in the back of seat plate to protect the connecting section of the needle body, the two front legs on the tail cover extends through the two dodging slots of the seat plate to the front; the front casing is located in the main cover, the flexible tenon of the front casing is in the first tenon stage of the main cover to limit the forward movement of the front casing in relative to the main cover, the foot hooks of the two front legs of the tail cover hook the flexible tenons of the front casing; the trigger tube is located in the front end of the main cover and extends out of the front end to protect the injection section of the needle body, the trigger tube is provided with a limit for forward movement in relative to the main cover, the rear part of the trigger tube is fixed on the seat rod of the needle base, the rear of the trigger tube is located in the front casing, the trigger tube is located in the third positioning position, the seat plate of the needle base is located in the first positioning position in relative to the main cover; the spring is against the stopper of the two front legs of the tail cover at one end and against the inner end face of the front casing at the other end;
    during the use and when the injection needle is installed to the insulin pen, the head of the insulin pen pushes the tail cover to move forward, the foot hook of the tail cover is lifted by the bevel of the convex of the front casing, and then passes over the convex, and the bevel of the tail cover presses the flexible tenon to bend inward to finally force the flexible tenon to unhook from the first tenon stage to release the limit of forward movement of the front casing in the main cover, and at the same time, the front casing is moved forward by the spring until the convex is stopped by the foot hook to limit the forward movement of the front casing; then, the cap of the tail cover contacts the seat plate of the needle base and pushes the seat plate to move forward from the first positioning position to the second positioning position, and as the trigger tube is limited by the forward movement limit, when the needle base moves forward, the trigger tube and the seat rod release the third positioning and form a sliding connection; then, when the frond end of trigger tube contact the skin of human body, the trigger tube moves backward and the insert of the trigger tube lifts the stopper on the tail cover to force the foot hook of the tail cover to gradually separate from the convex of the front casing until it's fully separated, so the front casing moves forward by the spring and extends through the front end of the main cover and the front end of front casing is blocked by the skin of human body and moves together with the front end of the trigger tube until the needle is penetrated into the skin to inject the insulin;

when the injection needle is pulled out from the skin after the use, the front casing is pushed out of the front end of the main cover by the spring until the convex of the front casing is stopped by the second tenon stage on the main cover, and at this time, the front casing is used to protect the injection section of the needle body; at the same time, the flexible tail fin of the front casing expands and is stuck in the anti-back slot of the main cover to form a limit for the backward movement of the front casing to prevent the returning of the front casing;

when the injection needle is removed from the head of the insulin pen after the use, the tail cover moves backward by the spring and the two stoppers on the tail cover hold the inserts of the trigger tube to move the trigger tube backward until the front end of the seat rod on the needle base contacts the inner end face of the trigger tube to stop; then the sharp tenon on the tail cover falls in the third tenon stage of the main cover to form a limit for forward movement of the tail cover, and the barbs of the inserts of the trigger tube match the stoppers to limit the backward movement of the tail cover in the back of the main cover, and at this time, the tail cover is used to protect the connecting section of the needle body and prevent the repeated use of the injection needle.

2. An insulin injection needle with needle tip protection includes:

a needle body, the needle body has an injection section extending in a forward direction, a connecting section extending in a rearward direction and a fixing section between the injection section and the connecting section;

a needle base, the needle base is used to fix the needle body and the fixing section of the needle body is fixed on the needle base, the injection section of the needle body extends from the front end of the needle base and the connecting section of the needle body extends from the rear end of the needle base;

a main cover, the main cover consists of the cylindrical structure in which the needle base and the needle body are located under assembly state, and the rear end of the main cover is connected to a insulin pen;

wherein:

the needle base consists of a seat plate, a seat rod and two front legs; and the seat rod is located in the front end of the seat plate and connected with the seat plate in a fixed way; the two front legs are arranged symmetrically at two sides of the seat rod and the roots of the two front legs are fixedly attached to the seat plate, and the inner side of each front leg is provided with a bevel at the root position, a stopper extending inward in the middle and a foot hook in the end position; and the outer edge of the seat plate matches with the inner edge of the main cover, and the outer edge of corresponding seat plate has a first positioning position and a second positioning position on the inner edge of the main cover with spacing in the axial direction; during the installation of the injection needle to the insulin pen, it uses the axial thrust of the insulin pen head to the seat plate to push the seat plate in the main cover to move from the first positioning position to the second positioning position in the axial direction to form a sliding positioning connection relationship between the needle base and the main cover; the outer edge of the seat plate in the first positioning position matches with the inner edge of the main cover through the first positioning structure and the outer edge of the seat plate in the second positioning position matches with the inner edge of the main cover through the second positioning structure; the first positioning structure is a concavo-convex positioning structure, an elastic positioning structure, or a frictional positioning structure; and the second positioning structure is a concavo-convex positioning structure, an elastic positioning structure, a friction positioning structure, a locking positioning structure or an end face abutment positioning structure;

the inner wall of main cover is provided with a first tenon stage in the middle, a second tenon stage in the front end and is provided with a anti-back slot in the forepart;

the main cover is provided with a front casing, a trigger tube and a spring;

the main structure of the front casing is a tubular body and the front casing is provided with an inner end face at the inner side of the front end; the front casing is provided with a flexible tenon extending backward and a flexible tail fin extending backward, and the flexible tenon and the flexible tail fin are arranged in a staggered way in the circumferential direction of the front casing; the front casing is provided with a convex extending outward at the outer side in the middle and the convex and the flexible tenon are in the corresponding position in the circumferential direction of the front casing;

the main structure of the trigger tube is a tubular body and the trigger tube is provided with two inserts extending backward at the rear end and the insert is provided with a barb; a recess is set between the tubular body of trigger tube and seat rod at one side and a convex is set at the other side and the recess contacts the convex to form a third positioning;

under assembly state before the use, the seat plate is located in the first positioning position in the main cover, and the two front legs on the seat plate extending forward extend to the front; the front casing is located in the main cover, and the flexible tenon of the front casing is in the first tenon stage of the main cover to limit forward movement of the front casing in relative to the main cover; the trigger tube is located in the front end of the main cover and extends out of the front end to protect the injection section of the needle body, and the trigger tube is provided with a limit position for forward movement in relative to the main cover, and the rear part of trigger tube is fixed on the seat rod of the needle base, the rear of the trigger tube is located in the front casing, the trigger tube is located in the third positioning position and the seat plate of the needle base is located in the first positioning position in relative to the main cover; the spring is against the stopper of the two front legs of the needle base at one end and against the inner end face of the front casing at the other end;

during the use and when the injection needle is installed to the insulin pen, the head of the insulin pen pushes the seat plate to move forward, and the bevel of the inner side of the front leg presses the flexible tenon to bend inward to finally force the flexible tenon to unhook from the first tenon stage to release the limit of the forward movement of the front casing in the main cover, and at the same time, the front casing is moved forward by the spring until the convex is stopped by the foot hook to limit the forward movement of the front casing; at the same time, the seat plate moves forward from the first positioning position to the second positioning position, and as the trigger tube is limited by the forward movement limit, when the needle base moves forward, the trigger tube and the seat rod release the third positioning and form a sliding connection; then, when the frond end of the trigger tube contact the skin of human body, the trigger tube moves backward and the insert of the trigger tube lifts the stopper on the front leg to force the foot hook of the front leg to gradually separate from the convex of the front casing until it's fully separated, so the front casing moves forward by the spring and extends through the front end of the main cover and the front end of front casing is blocked by the skin of human body and moves together with the front end of the trigger tube until the needle is penetrated into the skin to inject the insulin;

when the injection needle is pulled out from the skin after the use, the front casing is pushed out of the front end of the main cover by the spring until the convex of the front casing is stopped by the second tenon stage on the main cover, and at this time, the front casing is used to protect the injection section of the needle body; at the same time, the flexible tail fin of the front casing expands and is stuck in the anti-back slot of the main cover to form a limit for backward movement of the front casing to prevent the returning of the front casing, and finally the injection needle is removed from the head of the insulin pen.

3. The injection needle as claimed in claim 1, wherein: the concavo-convex positioning structure is formed by a groove provided in the circumferential direction of the outer edge of the seat plate and a protruding rib provided on the inner edge of the main cover.

4. The injection needle as claimed in claim 1, wherein: the elastic positioning structure is formed by matching of an elastic bead pin and a pitting; among the elastic bead pin and pitting, one is set in the outer edge of the seat plate and the other is set in the inner edge of the main cover.

5. The injection needle as claimed in claim 1, wherein: the friction positioning structure is formed by the friction matching of the outer edge of the seat plate and the inner edge of the main cover.

6. The injection needle as claimed in claim 1, wherein: the locking positioning structure is formed by the matching of the outer edge and the front and the rear of the seat plate and the slot at the inner edge of the main cover.

7. The injection needle as claimed in claim 1, wherein: the end face abutment positioning structure is formed by the abutment matching of the front end at the outer edge of the seat plate and the inner end face at the inner edge of the main cover.

8. The injection needle as claimed in claim 1, wherein: the main cover is provided with an outer sheath, which is a sleeve structure, and the outer sheath is installed at the outside of the main cover under the assembly state before use to protect the injection needle; the trigger tube is provided with a forward movement limit relative to the main cover, which is formed by the front end of the trigger tube being close to or abutted against the front inner end face of the outer sheath.

9. The injection needle as claimed in claim 2, wherein: the concavo-convex positioning structure is formed by a groove provided in the circumferential direction of the outer edge of the seat plate and a protruding rib provided on the inner edge of the main cover.

10. The injection needle as claimed in claim 2, wherein: the elastic positioning structure is formed by matching of an elastic bead pin and a pitting; among the elastic bead pin and pitting, one is set in the outer edge of the seat plate and the other is set in the inner edge of the main cover.

11. The injection needle as claimed in claim 2, wherein: the friction positioning structure is formed by the friction matching of the outer edge of the seat plate and the inner edge of the main cover.

12. The injection needle as claimed in claim 2, wherein: the locking positioning structure is formed by the matching of the outer edge and the front and the rear of the seat plate and the slot at the inner edge of the main cover.

13. The injection needle as claimed in claim 2, wherein: the end face abutment positioning structure is formed by the abutment matching of the front end at the outer edge of the seat plate and the inner end face at the inner edge of the main cover.

14. The injection needle as claimed in claim 2, wherein: the main cover is provided with an outer sheath, which is a sleeve structure, and the outer sheath is installed at the outside of the main cover under the assembly state before use to protect the injection needle; the trigger tube is provided with a forward movement limit relative to the main cover, which is formed by the front end of the trigger tube being close to or abutted against the front inner end face of the outer sheath.

* * * * *